United States Patent
Sun

(10) Patent No.: US 9,632,036 B2
(45) Date of Patent: Apr. 25, 2017

(54) IMAGE INSPECTION APPARATUS, IMAGE INSPECTION METHOD, IMAGE INSPECTION PROGRAM, COMPUTER-READABLE RECORDING MEDIUM AND RECORDING DEVICE

(71) Applicant: Keyence Corporation, Osaka (JP)

(72) Inventor: Zhuoli Sun, Osaka (JP)

(73) Assignee: Keyence Corporation, Osaka (JP)

( * ) Notice: Subject to any disclaimer, the term of this patent is extended or adjusted under 35 U.S.C. 154(b) by 71 days.

(21) Appl. No.: 14/716,901

(22) Filed: May 20, 2015

(65) Prior Publication Data

US 2015/0355101 A1 Dec. 10, 2015

(30) Foreign Application Priority Data

Jun. 9, 2014 (JP) ................................ 2014-119135

(51) Int. Cl.
*G01N 21/88* (2006.01)
*H04N 13/02* (2006.01)
*G06T 7/00* (2017.01)

(52) U.S. Cl.
CPC ....... *G01N 21/8806* (2013.01); *G06T 7/0004* (2013.01); *G06T 7/0073* (2013.01); *H04N 13/0207* (2013.01); *G01N 2201/06* (2013.01); *G06T 2207/10152* (2013.01); *G06T 2207/30164* (2013.01)

(58) Field of Classification Search
CPC ... G01N 21/8806; G06T 7/004; G06T 15/506; G06T 7/0073; H04N 13/0207; H04N 9/315
See application file for complete search history.

(56) References Cited

U.S. PATENT DOCUMENTS

| 8,454,871 B2* | 6/2013 | Schrunk | B44C 5/04 264/139 |
| 2004/0169652 A1* | 9/2004 | Herken | G06T 7/0053 345/426 |
| 2005/0030525 A1* | 2/2005 | Forster | G01B 11/2755 356/139.09 |

(Continued)

FOREIGN PATENT DOCUMENTS

JP 2007-206797 8/2007

*Primary Examiner* — Jingge Wu
(74) *Attorney, Agent, or Firm* — Kilyk & Bowersox, P.L.L.C.

(57) ABSTRACT

An image inspection apparatus includes: an imaging section for capturing an image of a workpiece from a certain direction; an illumination section for illuminating the workpiece from different directions at least three times; an illumination controlling section for sequentially turning on the illumination sections one by one; an imaging generating section for driving the imaging section to generate a plurality of images; a normal vector calculating section for calculating a normal vector with respect to the surface of the workpiece at each of pixels by use of a pixel value of each of pixels having a corresponding relation among the plurality of images; and a contour image generating section for performing differential processing in an X-direction and a Y-direction on the calculated normal vector at each of the pixels, to generate a contour image that shows a contour of inclination of the surface of the workpiece.

12 Claims, 28 Drawing Sheets

(56) References Cited

U.S. PATENT DOCUMENTS

| | | | | |
|---|---|---|---|---|
| 2007/0176927 A1* | 8/2007 | Kato | G06T 7/0073 | 345/426 |
| 2009/0226029 A1* | 9/2009 | Shimano | G06T 5/009 | 382/100 |
| 2011/0206237 A1* | 8/2011 | Saruta | G01B 11/00 | 382/103 |
| 2011/0304705 A1* | 12/2011 | Kantor | A61B 5/0059 | 348/49 |
| 2013/0120808 A1* | 5/2013 | Ichikawa | H04N 1/02865 | 358/475 |
| 2015/0355103 A1* | 12/2015 | Ando | G01N 21/8851 | 348/46 |
| 2015/0358602 A1* | 12/2015 | Mayumi | G06T 7/0073 | 348/46 |
| 2016/0098840 A1* | 4/2016 | Allano | G06T 7/0073 | 345/426 |

* cited by examiner

IMAGE INSPECTION APPARATUS, IMAGE INSPECTION METHOD, IMAGE INSPECTION PROGRAM, COMPUTER-READABLE RECORDING MEDIUM AND RECORDING DEVICE

CROSS-REFERENCE TO RELATED APPLICATIONS

The present application claims foreign priority based on Japanese Patent Application No. 2014-119135, filed Jun. 9, 2014, the contents of which is incorporated herein by reference.

BACKGROUND OF THE INVENTION

1. Field of the Invention

The present invention relates to an image inspection apparatus, an image inspection method, an image inspection program, and a computer-readable recording medium or a recording device, each using a photometric stereo method.

2. Description of Related Art

There has been used an image inspection apparatus for performing inspection of the presence or absence of a flaw on the surface of a workpiece (inspection target or subject), an external shape thereof, and reading of a printed character thereon. Such an image inspection apparatus performs necessary illumination on a workpiece, captures its image, and performs image processing such as edge detection on the obtained image data, to perform determination such as defective/non-defective determination based on a result of the processing.

However, in such an image inspection apparatus, there has been a case where the viewing easiness varies by a type of illumination or a direction of applying illumination, depending on a type of the workpiece. For this reason, performing appropriate inspection on such a workpiece has required sufficient information and experiences.

Further, in the conventional image inspection apparatus, erroneous inspection is apt to occur due to a small change in illumination condition, installation condition or the like, and stably performing inspection is difficult, which has been problematic. Further, in visual inspection of the workpiece, although both information on a shape of the workpiece such as a flaw and an edge, i.e., three-dimensional information, and planar information such as a printed character and a stain are inspection targets, those information cannot be detected well in some cases as a result of interference of the information, which has also been problematic.

As a technique for solving such problems, there is known an image processing apparatus for acquiring height information by a photometric stereo method (e.g., see Unexamined Japanese Patent Publication No. 2007-206797). Here, the photometric stereo method is one of techniques for three-dimensional measurement where an image is captured by illumination from a plurality of different illumination directions to find a normal vector of a workpiece from shadow information on the image. An image processing apparatus using such a photometric stereo method creates, from a normal vector (corresponding to an inclination image), an image with components on an X-axis and a Y-axis replaced by a luminance value or a reflectance image (corresponding to an albedo image), and applies the image to image inspection. Here, in order to accurately perform three-dimensional measurement by the photometric stereo method, consideration has been made mainly on a method for installation of an illumination device and a method for irradiation with illumination light.

However, in the image inspection by the photometric stereo method, since accurate information of a positional relation between a light source and a workpiece is required for calculating an accurate normal vector, for example when the surface on which the workpiece is placed is inclined from a horizontal plane or illumination is inclined, a number of major changes occur to cause deterioration in accuracy, which has been problematic.

Further, calculating an accurate normal vector requires a great number of images obtained by illumination in different directions, to take enormous amount of processing time, which has also been problematic. On the other hand, even when a height dimension of the workpiece cannot necessarily be accurately detected, it may be sufficient for use in inspection in many cases.

SUMMARY OF THE INVENTION

The present invention has been made in view of such problems, and a principal object is to provide an image inspection apparatus, an image inspection method, an image inspection program, and a computer-readable recording medium or a recording device, each of which allows easier inspection of a flaw and a printed character of a workpiece while keeping sufficient accuracy in a practical use by a photometric stereo method.

An image inspection apparatus according to one embodiment of the invention is an image inspection apparatus for performing visual inspection of a workpiece. The apparatus may include: three or more illumination sections for illuminating a workpiece from mutually different illumination directions; an illumination controlling section for turning on the three or more illumination sections one by one in a turning-on order; an imaging section for capturing an image of the workpiece from a certain direction at illumination timing for turning on each of the illumination sections by the illumination controlling section, to capture a plurality of partial illumination images with different illumination directions; a normal vector calculating section for calculating a normal vector with respect to the surface of the workpiece at each of pixels based on a photometric stereo method by use of a pixel value of each of pixels having a corresponding relation among the plurality of partial illumination images captured by the imaging section; and a contour image generating section for performing differential processing in an X-direction and a Y-direction on the normal vector at each of the pixels calculated by the normal vector calculating section, to generate a contour image that shows a contour of inclination of the surface of the workpiece. With the above configuration, differential processing is performed on a normal vector to generate a contour image that shows a contour of inclination of the surface of the workpiece, and this contour image is applied as an inspection target image, enabling image inspection that is hardly influenced by inclination of the workpiece or illumination, and is more robust to an environment than height measurement using the conventional photometric stereo.

Further, in an image inspection apparatus according to another embodiment of the invention, the contour image generating section may create a plurality of reduced inclination images with a different reduction ratio from the calculated normal vector at each of the pixels, perform differential processing in the X-direction and the Y-direction on each of the reduced inclination images, perform weighting such that a reduced contour image with a predetermined reduction ratio is reflected to the obtained reduced contour image to enlarge the image to an original size, and add all the enlarged reduced contour images to form a contour extraction image.

Further, in an image inspection apparatus according to still another embodiment of the invention, the weighting may be performed by preparing a previously decided weighting set, and applying the weighting set to the reduced contour image, to proportionally divide an adoption ratio of the reduced contour image with each of the reduction ratios.

Further, in an image inspection apparatus according to still another embodiment of the invention, the weighting set may include a set that makes large an adoption ratio of a reduced contour image by which a contour extraction image with clear roughness of the surface of the workpiece is obtained.

Further, in an image inspection apparatus according to still another embodiment of the invention, the weighting set may include a set that makes large an adoption ratio of a reduced contour image by which a contour extraction image suitable for OCR is obtained.

Moreover, an image inspection apparatus according to still another embodiment of the invention may further include: a texture extraction image generating section for calculating, from a normal vector at each of the pixels which exists in number corresponding to the number of times of illumination performed by the illumination sections and is calculated by the normal vector calculating section, albedos of each of the pixels in the same number as the number of the normal vectors, to generate from the albedos a texture extraction image that shows a design obtained by removing an inclined state of the surface of the workpiece, and the contour image generating section and the texture extraction image generating section can be switchable.

Further, in an image inspection apparatus according to still another embodiment of the invention, the texture extraction image generating section may sort values of the albedos of each of the pixels in the same number as the number of the normal vectors, and employ, as the texture extraction image, an image formed by adopting a pixel value in a specific order from the top.

An image inspection apparatus according to still another embodiment of the invention may further include: an inspection region specifying section for specifying a position of an inspection region to become an inspection target with respect to the generated contour image; an image processing section for performing image processing for detecting a flaw within the inspection region specified by the inspection region specifying section; and a determination section for determining the presence or absence of a flaw on the surface of the workpiece from a result of the processing by the image processing section.

Moreover, an image inspection apparatus according to still another embodiment of the invention may include: three or more illumination sections for illuminating a workpiece from mutually different illumination directions; an illumination controlling section for turning on the three or more illumination sections one by one in a turning-on order; an imaging section for capturing an image of the workpiece from a certain direction at illumination timing for turning on each of the illumination sections by the illumination controlling section, to capture a plurality of partial illumination images with different illumination directions; a normal vector calculating section for calculating a normal vector with respect to the surface of the workpiece at each of pixels by use of a pixel value of each of pixels having a corresponding relation among the plurality of partial illumination images captured by the imaging section; and a texture extraction image generating section for calculating, from a calculated normal vector at each of the pixels which exists in number corresponding to the number of times of illumination performed by the illumination sections, albedos of each of the pixels in the same number as the number of the normal vectors, to generate from the albedos a texture extraction image that shows a design obtained by removing an inclined state of the surface of the workpiece. The texture extraction image generating section may sort values of the albedos of each of the pixels in the same number as the number of the normal vectors, and employ, as the texture extraction image, an image formed by adopting a pixel value in a specific order from the top.

Further, in an image inspection apparatus according to still another embodiment of the invention, the imaging section and each of the illumination sections may be independent separate members, and may be arranged at arbitrary positions. With the above configuration, the illumination sections and the imaging section can be arranged in accordance with an actual workpiece and installation environment, enabling highly flexible installation with an enhanced degree of freedom in arrangement.

Further, in an image inspection apparatus according to still another embodiment of the invention, four illumination sections can be provided.

Further, in an image inspection apparatus according to still another embodiment of the invention, the three or more illumination sections are made up of a plurality of light-emitting elements arranged in an annular shape, and the illumination controlling section takes a predetermined number of adjacent light-emitting elements as a first illumination block, simultaneously turns on the light-emitting elements in the first illumination block, and turns off the other light-emitting elements, to make a first illumination section function as first illumination from a first illumination direction, performs control so as to turn on a second illumination block, which is made up of a predetermined number of light-emitting elements and adjacent to the first illumination block, to constitute the second illumination block for performing illumination from a second illumination direction different from the first illumination direction, and performs control so as to turn on a third illumination block, which is made up of a predetermined number of light-emitting elements and adjacent to the second illumination block, to constitute the third illumination block for performing illumination from a third illumination direction different from the first illumination block and the second illumination direction. With the above configuration, it is possible to divided illumination into three or more illumination blocks that function as three or more illumination sections by means of one illumination unit annularly arranged with a plurality of light-emitting elements, so as to further simplify the configuration of the illumination section.

An image inspection method according to one embodiment of the invention is an inspection method for capturing an image of a workpiece to perform visual inspection. The method includes the steps of illuminating a workpiece from three or more mutually different illumination directions by illumination sections, and capturing one partial illumination image with respect to each of the illumination directions by use of a common imaging section whose imaging direction and relative position with the illumination sections are adjusted in advance, to acquire a plurality of partial illumination images with different illumination directions; calculating a normal vector with respect to the surface of the workpiece at each of pixels by a normal vector calculating section by use of a pixel value of each of pixels having a corresponding relation among the plurality of partial illumination images with different illumination directions; performing differential processing in an X-direction and a Y-direction on the calculated normal vector at each of the pixels, to generate a contour image that shows a contour of inclination of the surface of the workpiece by a contour image generating section; and performing visual inspection of the workpiece by use of the contour image.

An image inspection method according to another embodiment of the invention is an image inspection program for capturing an image of a workpiece to perform visual inspection, and the program allows a computer to realize functions of illuminating a workpiece from three or more mutually different illumination directions by illumination sections, and capturing one partial illumination image with respect to each of the illumination directions by use of a common imaging section whose imaging direction and relative position with the illumination sections are adjusted in advance, to acquire a plurality of partial illumination images with different illumination directions; calculating a normal vector with respect to the surface of the workpiece at each of pixels by a normal vector calculating section by use of a pixel value of each of pixels having a corresponding relation among the plurality of partial illumination images with different illumination directions; performing differential processing in an X-direction and a Y-direction on the calculated normal vector at each of the pixels, to generate a contour image that shows a contour of inclination of the surface of the workpiece by a contour image generating section; and performing visual inspection of the workpiece by use of the contour image.

Further, a computer-readable recording medium or a recording device of the present invention store the image inspection program. The recording medium includes a magnetic disk, an optical disk, a magneto-optical disk, a semiconductor memory, and other program-storable medium, such as a CD-ROM, a CD-R, a CD-RW, a flexible disk, a magnetic tape, an MO, a DVD-ROM, a DVD-RAM, a DVD-R, a DVD+R, a DVD-RW, a DVD+RW, a Blu-ray (product name), and an HD-DVD (AOD). Further, the program is distributed by downloading through a network such as the Internet, other than stored into the above recording medium. Moreover, the recording device includes a general-purpose or special-purpose device where the program is mounted in the form of software, firmware or the like, in an executable state. Furthermore, each processing and each function included in the program may be executed by program software that is executable by the computer, and processing of each part may be realized by predetermined hardware such as a gate array (FPGA, ASIC) or in the form of program software being mixed with a partial hardware module that realizes some element of hardware.

DETAILED DESCRIPTION OF PREFERRED EMBODIMENTS

Hereinafter, embodiments of the present invention will be described with reference to the drawings. The embodiments shown below are for embodying technical ideas of the present invention, and the present invention is not limited to the following. Further, the present specification does not limit members shown in the claims to members of the embodiments. Especially, dimensions, materials, shapes, relative disposition and the like of constituent components described in the embodiments are not intended to restrict the scope of the present invention thereto, but are mere explanatory examples, unless particularly specifically described. It is to be noted that sizes, positional relations and the like of members shown in each drawing may be exaggerated for clarifying a description. Further, in the following description, the same name or symbol denotes the same member or members of the same quality, and a detailed description thereof will be omitted as appropriate. Moreover, each element constituting the present invention may have a mode where a plurality of elements are made up of the same member and the one member may serve as the plurality of elements, or conversely, a function of one member can be shared and realized by a plurality of members.

(1. Configuration of Image Inspection Apparatus 1)

Figure 1:
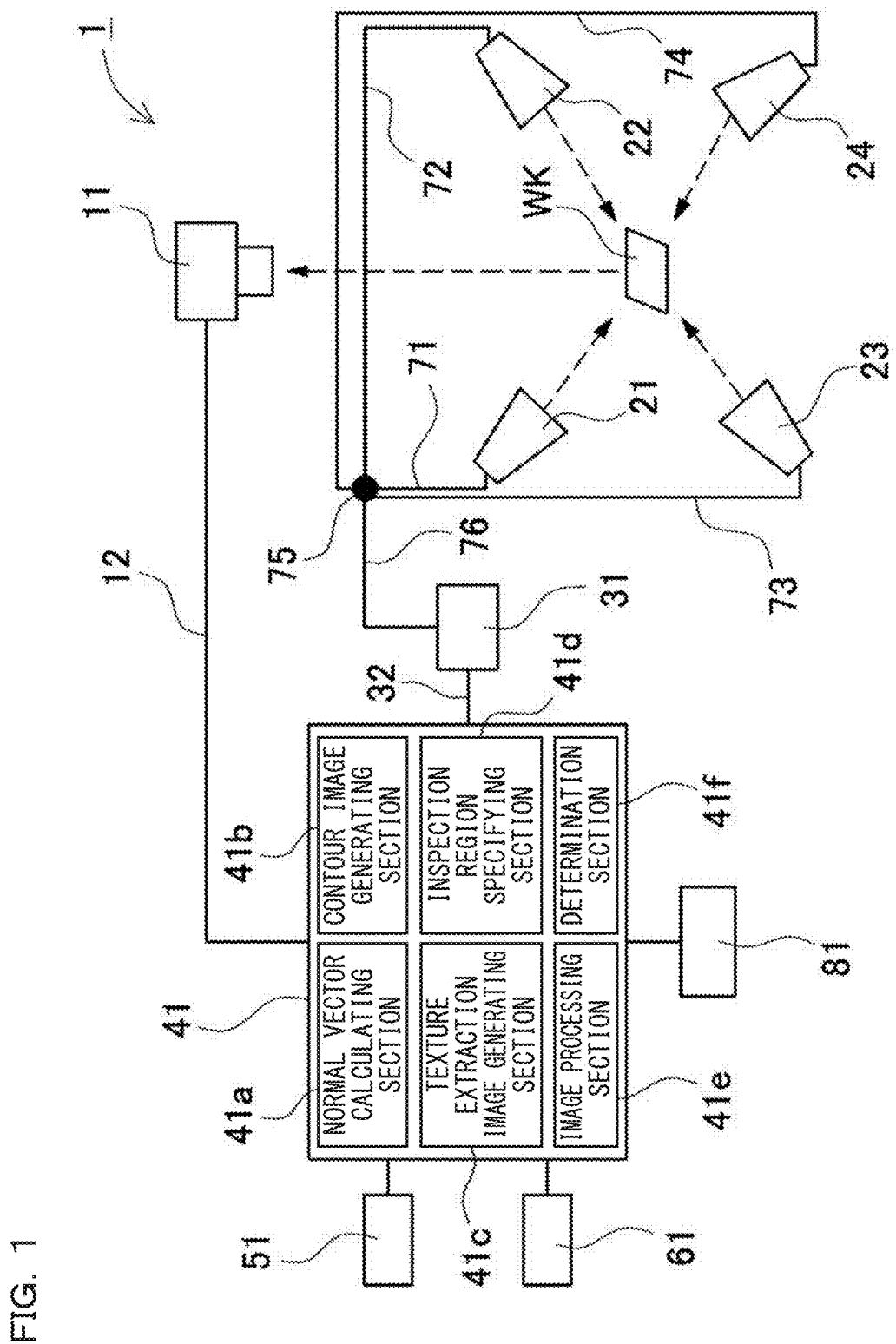
FIG. 1 is a block diagram showing a configuration of an image inspection apparatus according to a first embodiment of the present invention.

FIG. 1 shows a block diagram of an image inspection apparatus according to a first embodiment of the present invention. The image inspection apparatus 1 shown in this drawing includes: an imaging section 11 that captures an image of an inspection target (hereinafter also referred to as "workpiece WK") from a certain direction; illumination sections for illuminating the workpiece WK from three or more different illumination directions; an illumination controlling section 31 for turning on each of the illumination sections one by one in a turning-on order; and an image processing part 41 that is connected with the illumination controlling section and the imaging section to control these sections. The image processing part 41 and the imaging section are connected via an image capturing cable 12, and the image processing part 41 and the illumination controlling section 31 are connected via an illumination cable 32. Further, the image processing part connects a display section 51 and an operation section 61. Moreover, the image processing part can also be connected with a PLC (Programmable Logic Controller), a computer and the like as external devices, according to the need.

The imaging section captures an image of the workpiece WK from a certain direction at illumination timing for turning on each of the illumination sections by the illumination controlling section, to capture a plurality of partial illumination images with different illumination directions.

The image processing part realizes functions of a normal vector calculating section 41a, a contour image generating section 41b, a texture extraction image generating section 41c, an inspection region specifying section 41d, an image processing section 41e, and a determination section 41f. The normal vector calculating section 41a calculates a normal vector n with respect to the surface of the workpiece WK at each of pixels by use of a pixel value of each of pixels having a corresponding relation among the plurality of partial illumination images captured by the imaging section. The contour image generating section 41b performs differential processing in an X-direction and a Y-direction on the calculated normal vector n at each of the pixels, to generate a contour image that shows a contour of inclination of the surface of the workpiece WK. The texture extraction image generating section 41c calculates, from the calculated normal vector n at each of the pixels which exists in number corresponding to the number of times of illumination performed by the illumination sections, albedos of each of the pixels in the same number as the number of the normal vectors n, to generate from the albedos a texture extraction image that shows a design obtained by removing an inclined state of the surface of the workpiece WK. The inspection region specifying section 41d specifies a position of an inspection region to become an inspection target with respect to the generated contour image. The image processing section 41e performs image processing for detecting a flaw within the specified inspection region. The determination section 41f determines the presence or absence of a flaw on the surface of the workpiece WK based on the processing result.

The imaging section and the illumination section can be arranged as separate members. This allows a layout with a high degree of freedom. As one example shown in a schematic plan view of FIG. 2 and a schematic side view of FIG. 3, the imaging section 11 with an optical axis turned in a vertical direction is arranged immediately above the workpiece WK placed on a stage SG. Further, four illumination sections, namely a first illumination section 21, a second illumination section 22, a third illumination section 23 and a fourth illumination section 24, are arranged at the same height in the cardinal directions of north, south, east and west of the imaging section 11. A positional relation between the imaging section and each of the illumination sections having been arranged are recorded on the image inspection apparatus. Each of the illumination sections is sequentially turned on at predetermined illumination timing by the illumination controlling section, and an image of the workpiece is captured from a certain direction by the common imaging section, to acquire partial illumination images.

The configuration where the imaging section and the illumination section are separate members is not restrictive, and these may be integrally configured via an arm or the like.

In this case, since the positional relation between the imaging section and each of the illumination sections is fixed in advance, an adjustment operation such as matching of the optical axes can be made unnecessary. However, the degree of freedom will be lost.

(Imaging Section)

As for the imaging section 11, for example, an image capturing element such as a CCD (Charge Coupled Device) camera or a CMOS (Complementary Metal Oxide Semiconductor) imager can be used. The image capturing element performs photoelectric conversion on an image of a subject to output an image signal, and a signal processing block converts the outputted image signal to a luminance signal and a color difference signal, to output the signals to the image processing part 41 connected by the image capturing cable 12.

(Illumination Section)

Figure 2:
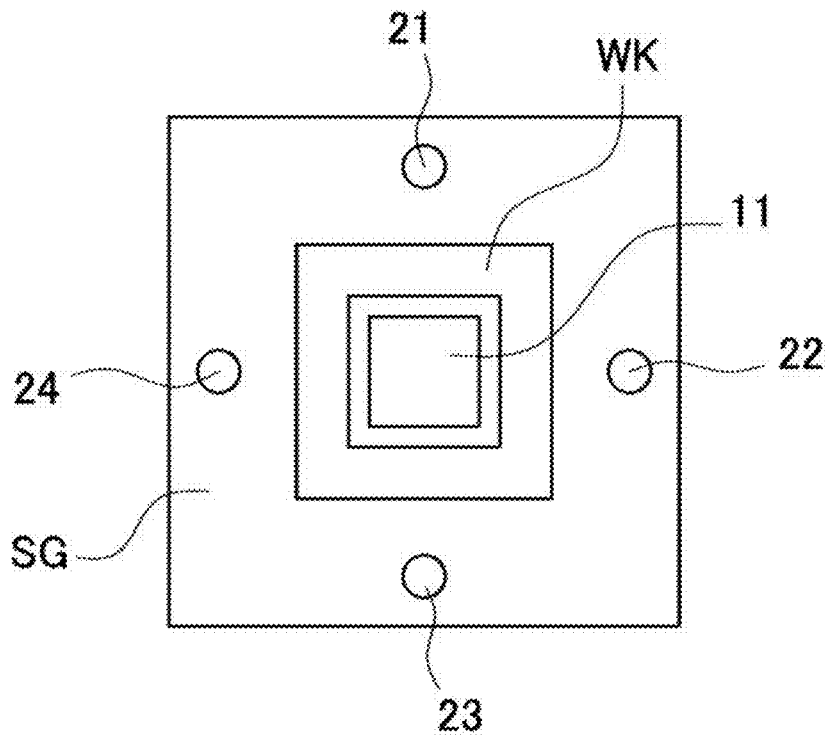
FIG. 2 is a schematic plan view showing a positional relation between an imaging section and each of illumination sections of the image inspection apparatus of FIG. 1.

The illumination sections 21, 22, 23, 24 are arranged so as to surround the workpiece WK as shown in the schematic plan view of FIG. 2 such that the workpiece WK can be irradiated with illumination light from different illumination directions. Further, as shown in the schematic side view of FIG. 3, each of the illumination sections is arranged with the optical axis turned obliquely below. It is preferable to match the optical axis of the imaging section with a central axis of a plane (imaginary rotational plane) provided with the illumination sections so that an image of the workpiece illuminated by each of the illumination sections can be captured by the common imaging section. Further, it is preferable to set an interval (azimuth from the central axis) between the illumination sections by uniformly dividing 360° by the number of illumination sections. Moreover, it is preferable to make a zenith angle constant in all the illumination sections. Furthermore, it is also preferable to make a distance between each of the illumination sections and the workpiece constant. This can simplify input of information on the azimuth and the zenith angle which are required for computing in photometric stereo processing. Further, as described later, since an entirely turning-on image MC is captured in an entirely turning-on state where all the illumination sections are on, imaging can be performed in an illumination state with little unevenness just by uniformly reducing the intensity of the entire illumination with the above configuration.

In the example of FIG. 1, the illumination sections are made up of four sections: the first illumination section 21, the second illumination section 22, the third illumination section 23 and the fourth illumination section 24. For each of the illumination sections, an incandescent light bulb, a fluorescent lamp or the like can be used. In particular, a semiconductor light-emitting element such as a light emitting diode (LED) is preferable as having small power consumption, a long life and excellent responsiveness. As shown in FIG. 1, the illumination sections are connected to an illumination dividing unit 75 via the respective cables 71, 72, 73, 74, and are further connected to the illumination controlling section 31 via a cable 76.

(Illumination Dividing Unit)

The illumination dividing unit is an interface for connecting each of the illumination sections and the illumination controlling section. Specifically, an illumination connector for connecting the illumination cable extending from the illumination section is provided. In the example of FIG. 1, four illumination connectors are provided so as to connect the four illumination sections. Here, in order to correctly connect the illumination cable to the illumination connector, a mark or the like may be provided as an installation auxiliary section (detailed later). Correctly connecting the illumination cable of each of the illumination sections to the illumination connector of the illumination dividing unit allows the illumination section to be turned on from a correct direction in a correct order by the illumination controlling section, and further, operating the imaging section in synchronization with each illumination timing allows the partial illumination image to be captured. In addition, although the illumination dividing unit is provided as a separate body from the illumination controlling section in the example of FIG. 1, this configuration is not restrictive, and for example, the illumination dividing unit may be incorporated into the illumination controlling section.

An illumination color of each of the illumination sections 21, 22, 23 24 can also be changed in accordance with a type of the workpiece WK. For example, when a small flaw is to be inspected, blue illumination with a short wavelength is preferable. When a colored workpiece is to be inspected, white illumination is preferably used so that the color of the illumination does not become obstructive. When oil is on the workpiece, red illumination may be adopted for preventing an influence thereof.

Figure 3:
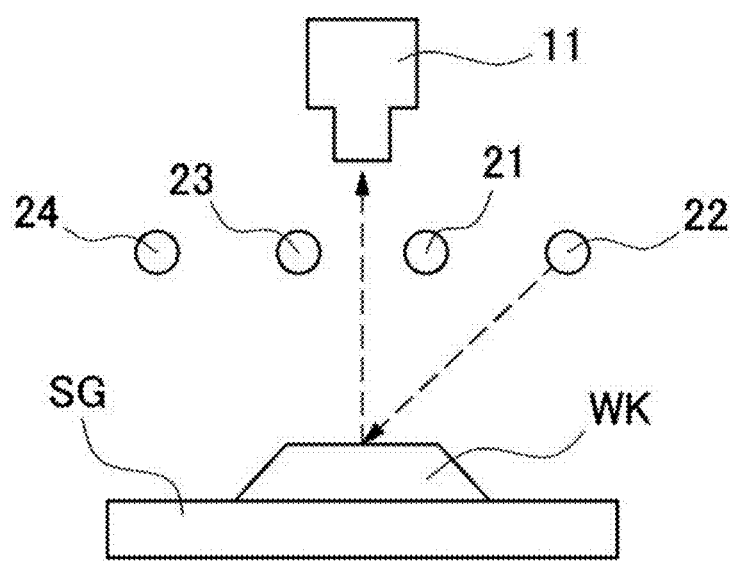
FIG. 3 is a schematic side view showing the positional relation between the imaging section and each of the illumination sections of the image inspection apparatus of FIG. 1.

Although the number of illumination sections is four in the example of FIGS. 1 to 3, at least three illumination sections can be sufficiently used so as to allow the workpiece WK to be illuminated from three or more different illumination directions. When the number of illumination sections is increased, the partial illumination images from more illumination directions can be obtained, and hence the accuracy in image inspection can be improved. For example, directions of northeast, northwest, southeast and southwest may be added and a total of eight illumination sections may be arranged. Further, it is preferable to set an interval (azimuth from the central axis) between the illumination sections by uniformly dividing 360° by the number of illumination sections. Moreover, it is preferable to make a zenith angle constant in all the illumination sections. It is to be noted that an increase in number of images to be processed leads to an increase in processing amount, which slows the processing time. In the present embodiment, in view of balance of the processing speed, the easiness to perform the arithmetic processing, the accuracy and the like, the number of illumination sections is set to four as described above.

Figure 4:
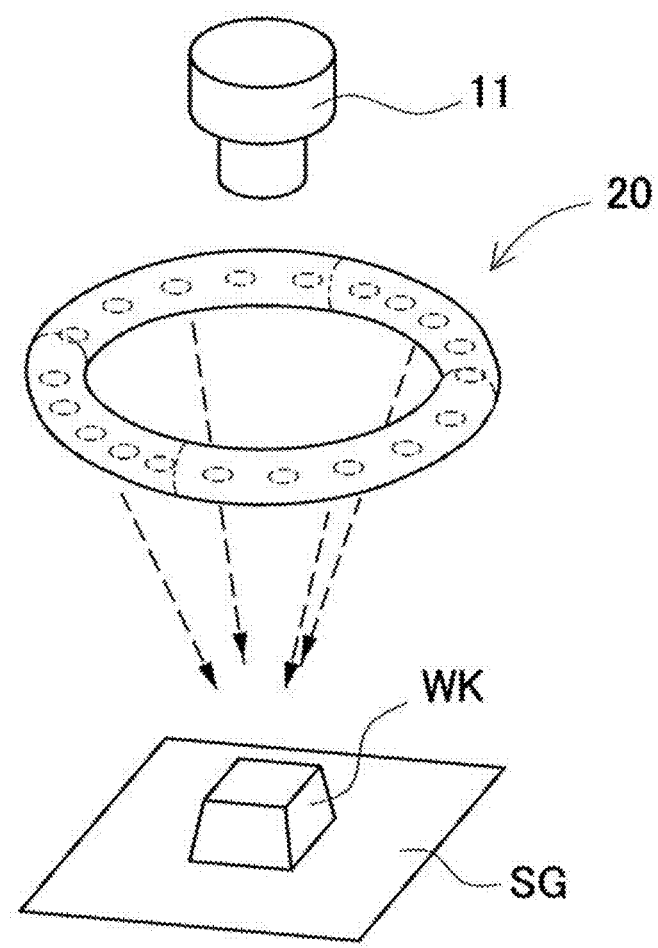
FIG. 4 is a schematic view showing an illumination section that realizes four illumination blocks according to a second embodiment.

Further, the illumination section can also be made up of a plurality of annularly arranged light-emitting elements. For example, in ring illumination according to a second embodiment shown in FIG. 4, annularly arranged light-emitting elements are divided into four illumination blocks. Then, the illumination controlling section takes a first illumination block as the first illumination section, a second illumination block as the second illumination section, a third illumination block as the third illumination section and a fourth illumination block as the fourth illumination section, and makes illumination timing for the respective illumination blocks different, thereby allowing control in a similar manner to the case of four separate illumination sections existing.

Figure 5:
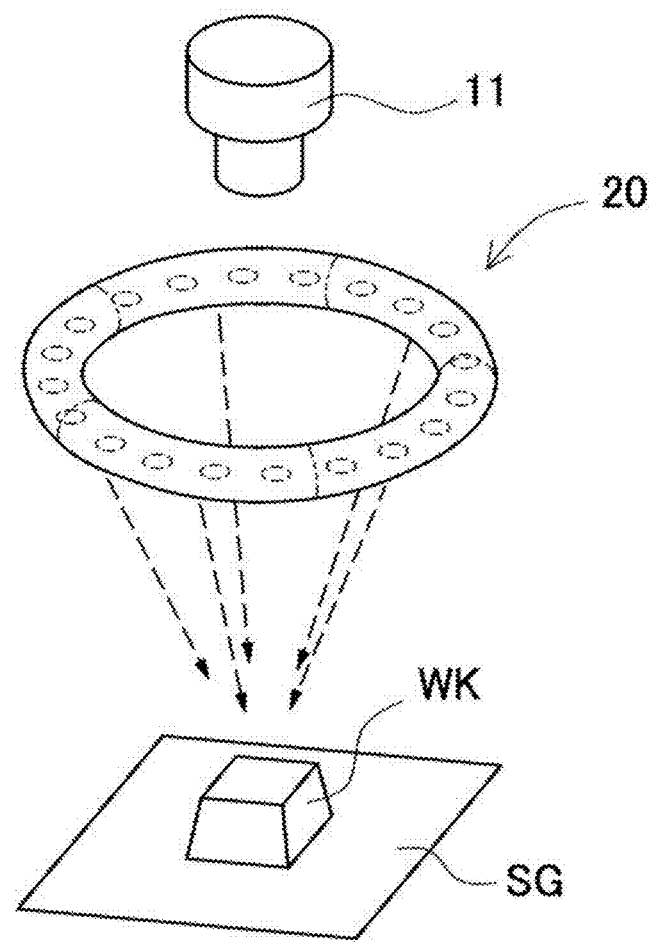
FIG. 5 is a schematic plan view showing a state where five illumination blocks are realized by the illumination section of FIG. 4.

Further, with this configuration, there can be obtained an advantage that the number of illumination sections can be arbitrary changed by use of the same ring illumination. That is, when turning-on of each of the light-emitting elements can be arbitrarily controlled by the illumination controlling section, as shown in FIG. 5, the number of illumination blocks obtained by dividing the circumference of the annularly arrayed light-emitting elements is changed from four to five, and the illumination controlling section performs control so as to capture each of partial illumination images by shifting the illumination timing for turning on each of the five illumination blocks. Thus, it is possible to acquire partial illumination images from five illumination directions. Further, similarly, when the annular circumference is divided into six or seven blocks, the illumination directions can further be increased. Moreover, the configuration where partial illumination images are constantly acquired by certain illumination blocks is not restrictive, and illumination blocks may be changed in each cycle. As thus described, by adjusting the turning-on pattern of each of the light-emitting elements, it is possible to virtually change the number of illumination blocks by use of the same one ring illumination, so as to obtain a similar effect to that obtained by adjusting the number of illumination sections. In other words, it is possible to deal with different accuracies by means of the common hardware.

Figure 6:
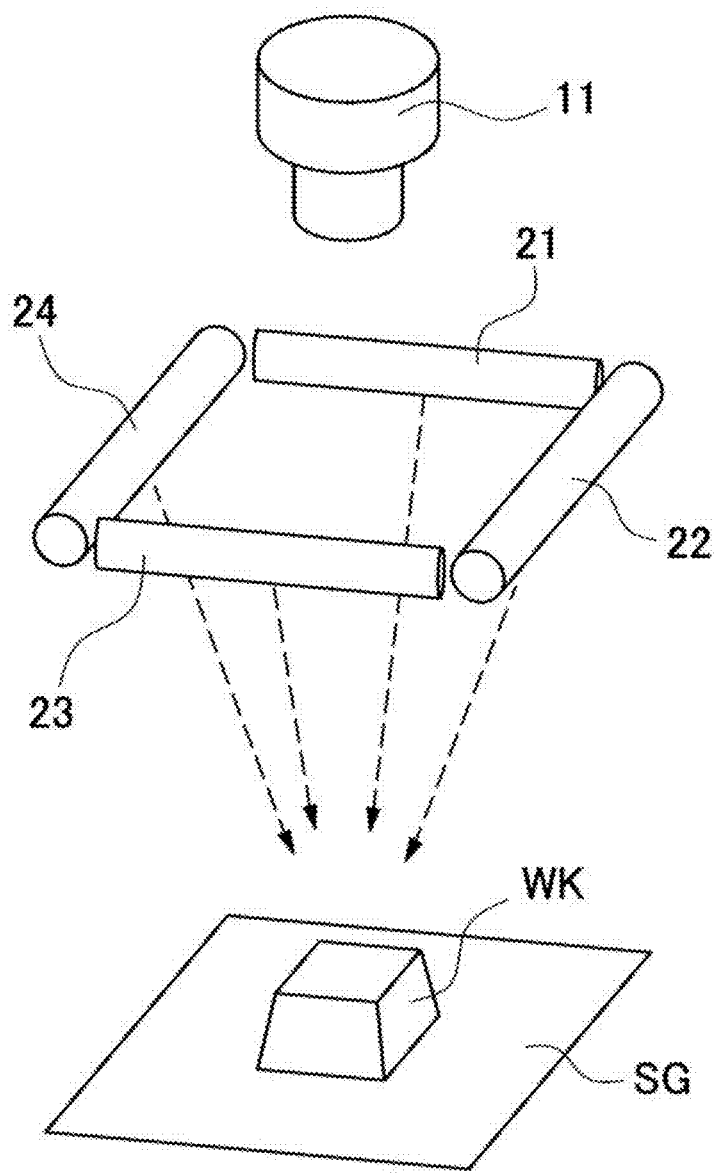
FIG. 6 is a schematic plan view showing illumination sections according to a third embodiment.
Figure 7:
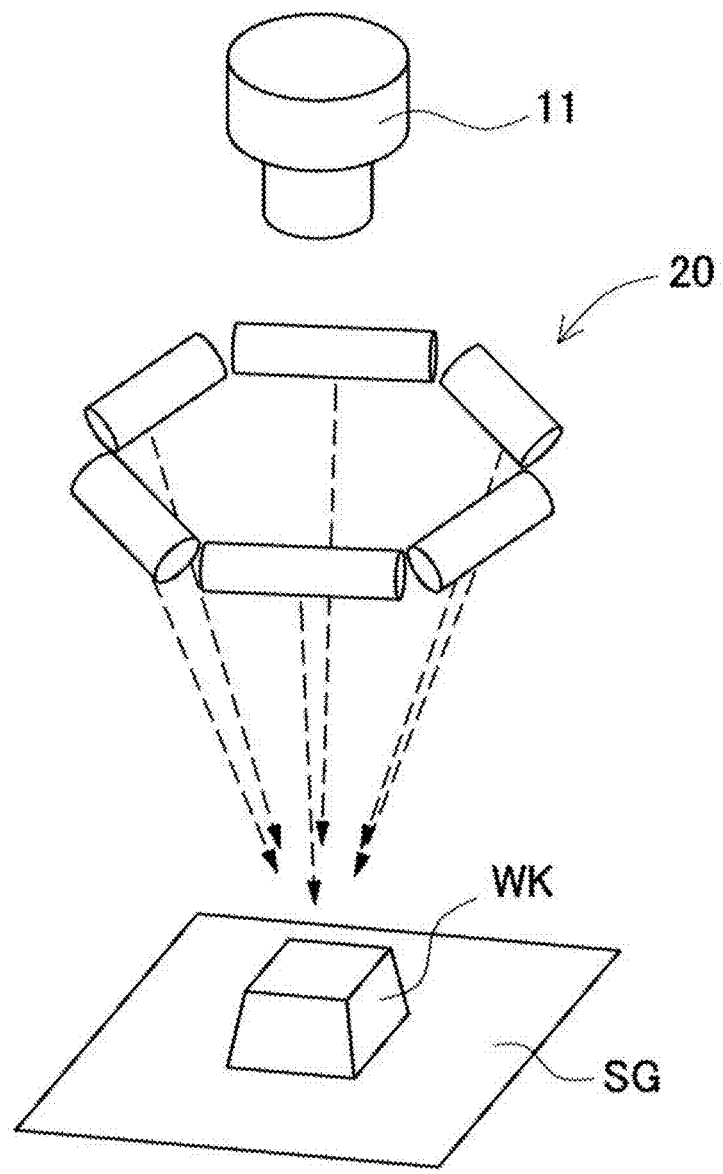
FIG. 7 is a schematic plan view showing illumination sections according to a fourth embodiment.

Further, other than arranging the illumination sections in the annular form, it is also possible to arrange illumination sections, each of which is configured in a bar shape, in a rectangular form as a third embodiment as shown in a schematic plan view of FIG. 6, or it is also possible to arrange illumination sections in a polygonal form as a fourth embodiment as shown in a schematic plan view of FIG. 7.

Figure 8:
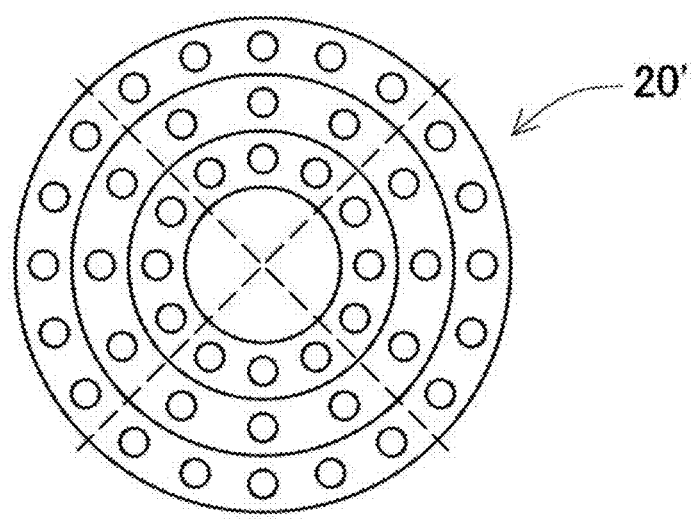
FIG. 8 is a schematic plan view showing an illumination section according to a modified example.
Figure 9:
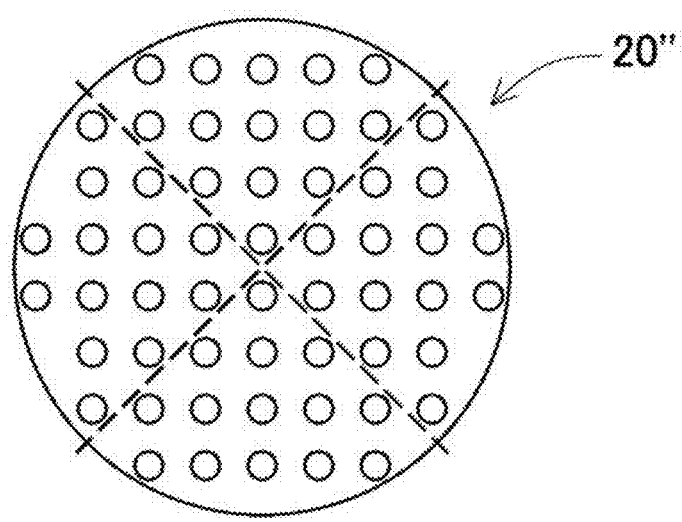
FIG. 9 is a schematic plan view showing an illumination section according to another modified example.

Alternatively, it is also possible to arrange the illumination sections in a flat form other than being arranged in a circular or polygonal annular form. For example, a large number of light-emitting elements are arranged in a flat form and an illumination block to be turned on is changed, thereby allowing realization of different illumination directions. Specifically, as an illumination section according to a modified example shown in FIG. 8, an illumination unit 20' obtained by superimposing concentrically annular rings is configured, and the illumination section is configured by the annular rings with different radiuses as respective illumination blocks. Alternatively, as an illumination section according to another modified example shown in FIG. 9, an illumination unit 20" obtained by arraying light-emitting elements in a dot-matrix form may be configured, and the illumination section may be configured by illumination blocks obtained by dividing the illumination unit by a plurality of line segments passing through its center. As thus described, the illumination section and the illumination direction in the present invention are not restricted to physically separated illumination, but are used in the meaning of including a configuration where illumination is performed by means of illumination blocks obtained by dividing one illumination section into a plurality of blocks.

It is to be noted that in the present example, the processing is performed on the assumption that partial illumination light by each of the illumination sections is parallel light within an imaging range. So long as the partial illumination light is parallel light, only the direction of the illumination light (e.g., any of north, south, east and west) is a concern, and other detailed positions, such as a coordinate position of a light source of the illumination section, are not required to be considered.

(Illumination Controlling Section)

The illumination controlling section performs control so as to turn on three or more illumination sections one by one in a turning-on order and synthesize each of the illumination sections and the imaging section such that an image of the workpiece is captured by the imaging section from a certain direction at illumination timing for turning on each of the illumination sections. In other words, the illumination controlling section synthesizes the timing for illumination by the illumination section with the timing for imaging by the imaging section. Further, the turning-on order in which the illumination controlling section turns on each of the illumination sections may be such that the illumination sections arranged to surround the workpiece are turned on in a clockwise order or a counterclockwise order, or in a discrete order such as an alternate order or a crossing order. Whatever the order is, it is possible to construct a normal vector image by the photometric stereo method, by grasping an illumination direction of illumination by which a partial illumination image has been captured at each illumination timing.

Figure 10:
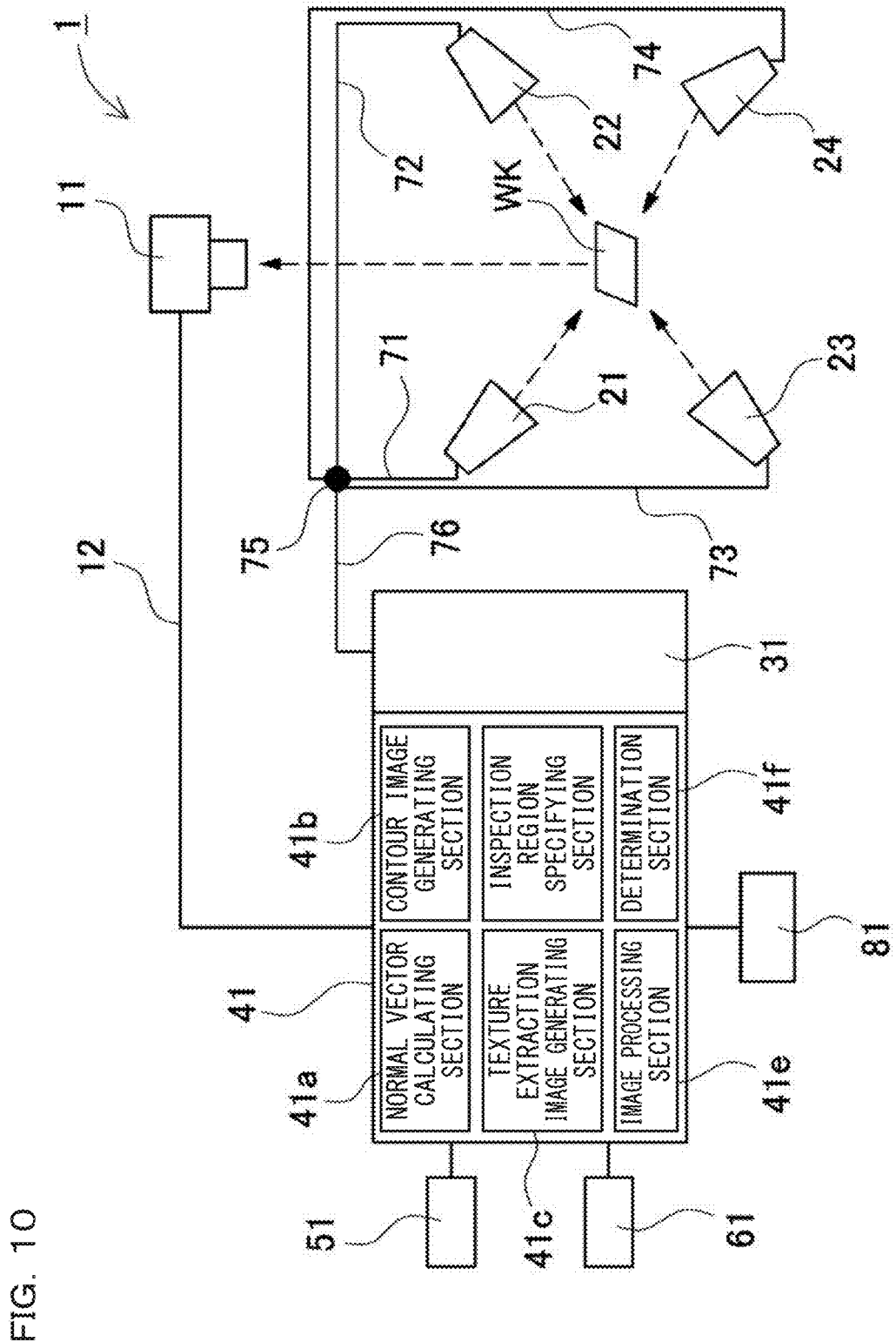
FIG. 10 is a schematic view showing a configuration of an image inspection apparatus according to a fifth embodiment.
Figure 11:
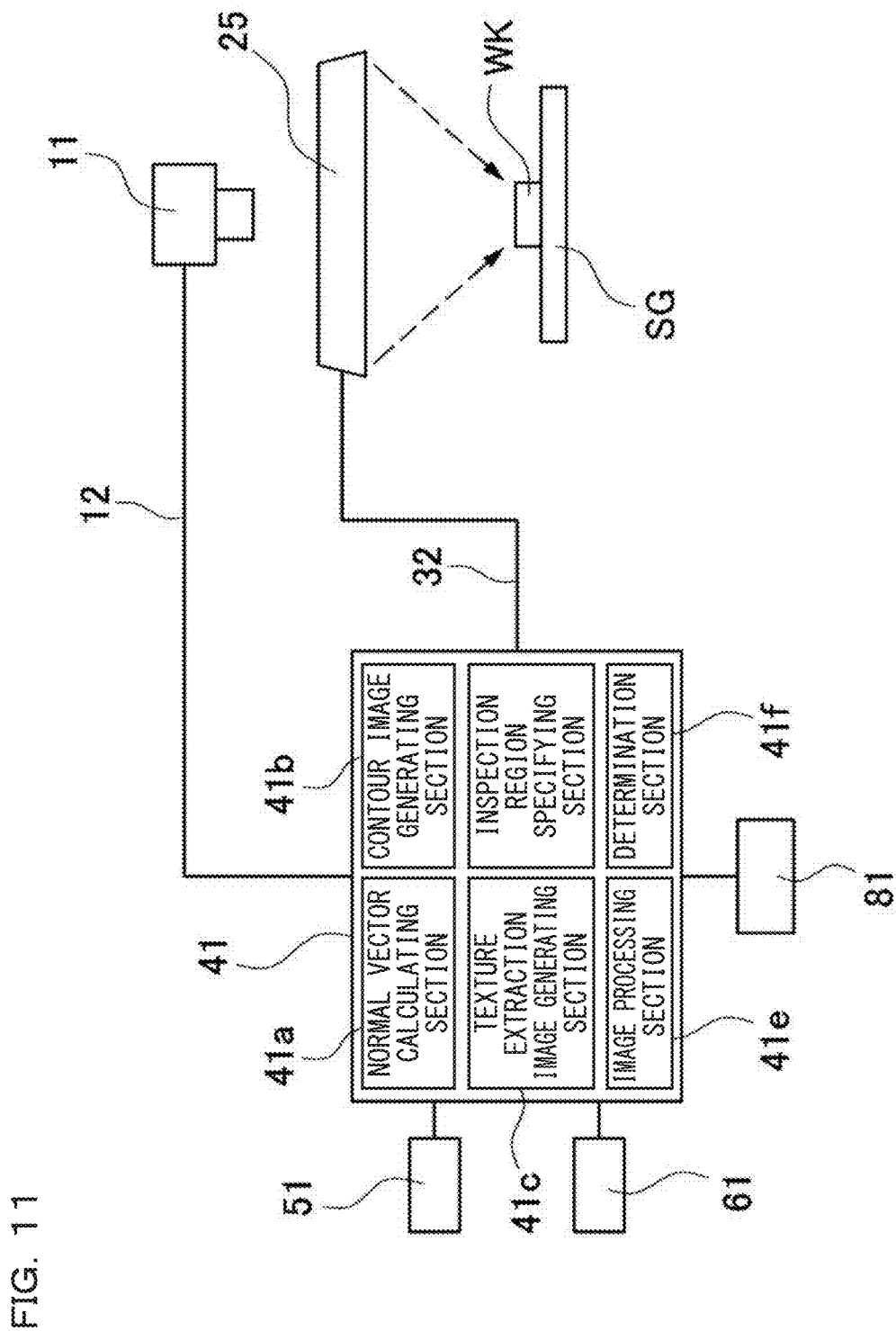
FIG. 11 is a schematic view showing a configuration of an image inspection apparatus according to a sixth embodiment.

It is to be noted that in the first embodiment of FIG. 1, the illumination controlling section 31 is provided as a separate body from the image processing part 41, but this configuration is not restrictive. For example, the illumination controlling section 31 may be integrated with the image processing part 41 as in a fifth embodiment shown in FIG. 10, or it may be built in an illumination section 25 as in a sixth embodiment shown in FIG. 11.

(Image Processing Part)

The image processing part 41 controls operations of the imaging section 11 and the illumination sections 21, 22, 23, 24. Further, by use of image signals Q1 to Q4 of four partial illumination images inputted from the imaging section 11, the image processing part 41 generates a normal vector image (hereinafter referred to as "inclination image") on a plane at each pixel, and creates, from the inclination image, a secondary inclination image (hereinafter referred to as "contour extraction image") in the X-direction and the Y-direction and an albedo (meaning a reflectance) image (hereinafter also referred to as "texture extraction image"). Then, by use of those images, the image processing part 41 performs processing for inspecting a flaw, detecting a character, or the like. It should be noted that the processing for inspecting a flaw, detecting a character, or the like is not restricted to the configuration where the processing is performed in the image processing part 41, and for example, it can be executed on the external device side such as a PLC 81.

Figure 12:
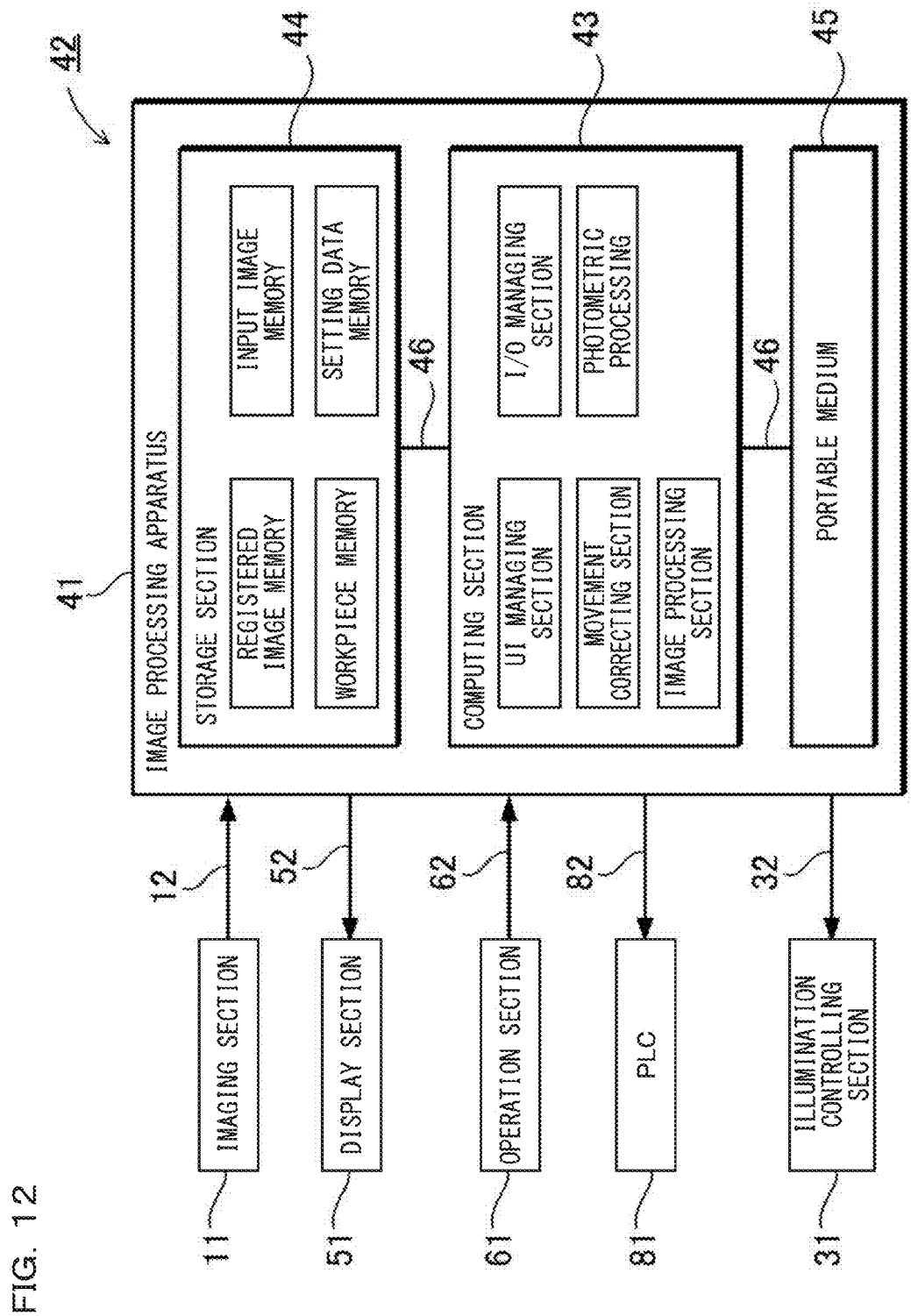
FIG. 12 is a block diagram for use in explaining a signal processing system of an image processing section.

FIG. 12 shows a signal processing system 42 of the image processing part 41. The signal processing system 42 is made up of a CPU 43, a memory 44, a ROM 45, a display section 51, an operation section 61 such as a pointing device, the imaging section 11, the illumination controlling section 31, and a PLC (program logic controller) 81 for executing result output processing, and these are mutually connected via a bus 46 and cables 12, 32, 52, 62 and 82. It is to be noted that the ROM 45 may be a portable medium. Further, the display section 51 may be used together with the operation section 61 by forming a touch panel or the like.

Based on a program stored in the ROM 45, the CPU 43 controls transmission and reception of data among the memory 44, the ROM 45, the display section 51, the operation section 61, the imaging section 11, the illumination controlling section 31 and the PLC 81, and controls the display section 51, the imaging section 11 and the illumination controlling section 31.

Although the image processing part 41 is assumed to be, for example, one computer stored with a program, but each section may be configured by combination of a plurality of computers, or part of the sections may be configured of a dedicated circuit. Alternatively, the image processing part 41 can be a dedicatedly designed member such as an ASIC.

(Determination Section)

The image processing part 41 realizes the function of the determination section as described above. The determination section inspects the presence or absence of a flaw or a size of the flaw based on the obtained texture extraction image. For example, when the obtained value is not smaller than a predetermined threshold, determination as a flaw is made. Further, according to the need, the determination section can also perform OCR based on a contour extraction image, to output a recognized character string.

(Basic Principle)

Next, by use of the above image inspection apparatus, a basic principle in performing visual inspection of the workpiece will be described while it is compared with the technique of Unexamined Japanese Patent Publication No. 2007-206797 as the conventional technique. First, a basic principle of the technique disclosed in Unexamined Japanese Patent Publication No. 2007-206797 is that, by use the principle of the photometric stereo method, light is applied to an unknown surface from a variety of directions and the shape of the workpiece is estimated using differences in reflective light of the workpiece. The reflective light of the workpiece is affected by an incident angle of illumination, a distance from illumination and the like, and has a property that the light is brightest when the incident angle is 90° and the light becomes darker as the distance from the illumination becomes longer.

With this property, a plurality of illuminations whose brightness and positions are known are prepared and turning-on of the illumination is sequentially switched, to estimate in which direction the surface is turned by use of a difference in brightness of the reflective light at the time of irradiation with light from the illumination in each direction. Specifically, an X-component image obtained by replacing the X-component and the Y-component of the inclination image with luminance of the X-component, and a Y-component image obtained by replacing the X-component and the Y-component of the inclination image with luminance of the Y-component are to be created and applied to inspection.

However, this method has a problem of inferior robust characteristics because an obtained inspection image greatly changes by slight inclination of the illumination or the installation surface of the workpiece, or an error of input information such as an originally inputted illumination position. For example, the method has a disadvantage that an inspection image corresponding to an actual shape of the workpiece can not necessarily be obtained, as seen in a case where an image of roughness is obtained although there actually is no roughness, and a case where an image in which the center of the workpiece is swelled due to a change in brightness is seen while a closer position of an image to illumination is normally seen more brightly.

In contrast, a basic principle of the image inspection technique according to the present embodiment is as follows. Although a primary inclination image is generated by the photometric stereo method at first, a secondary inclination image, namely a contour extraction image is created by performing differential processing on the generated primary inclination image in the X-direction and the Y-direction, and inspection of a flaw and the like is performed with that image. Even in the case of occurrence of the foregoing disadvantage, the influence on the secondary inclination image is small, and by setting a place with a large change in surface inclination to have a dark tone and setting a place with a small change in surface inclination to have a bright tone, the secondary inclination image becomes a preferable image for extracting a flaw, a contour and the like where the inclination of the surface of the workpiece greatly changes.

Further, in the technique disclosed in Unexamined Japanese Patent Publication No. 2007-206797, halation occurs in the reflectance image (corresponding to the texture extraction image) generated by the photometric stereo method, and it may be difficult to detect a character, and the like. In contrast, in the image inspection technique according to the present embodiment, by use of the basic principle that halation basically does not occur in the same place unless two illuminations are used, for example, the third largest pixel value of four pixel values is adopted at each pixel, to remove an influence of halation.

Additionally, in the image processing apparatus disclosed in Unexamined Japanese Patent Publication No. 2007-206797, the camera and the light source for illumination are integrally configured, but with this configuration, the camera and the light source increase in size, and at the time of installation, those are restricted in size, which has been problematic. In contrast, in the image inspection apparatus according to the present embodiment, the imaging section and the illumination section can be made to be separate members, to allow more flexible installation in view of an arrangement space, which is also an advantage in terms of usability.

(Basic Principle of the Photometric Stereo Method)

Figure 13A:
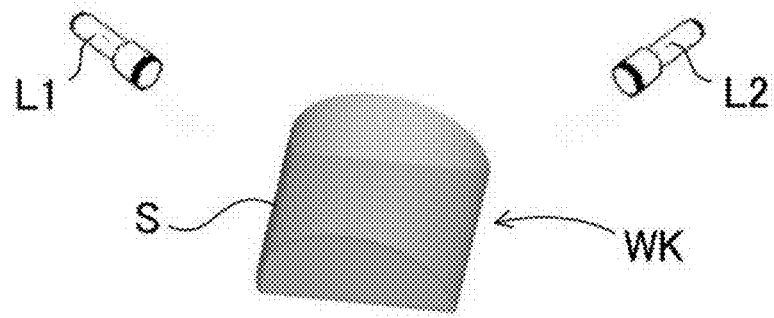
FIG. 13A is a view showing a positional relation between a diffusing reflective surface S and illumination.
Figure 13B:
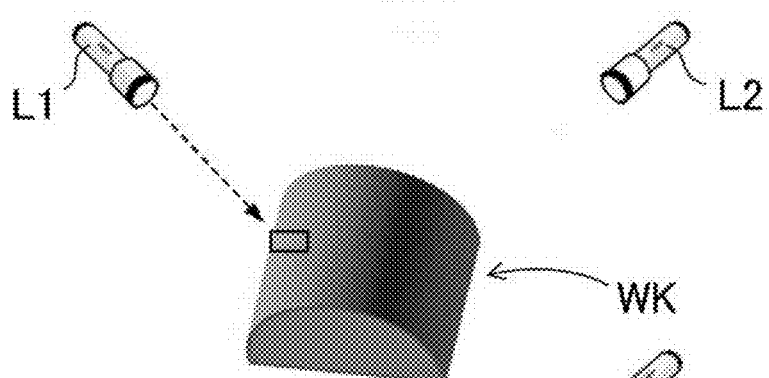
FIG. 13B is a view showing a state where irradiation is performed with light from L1.

Here, the basic principle of the photometric stereo method will be described with reference to FIGS. 13A to 13D. First, as shown in FIG. 13A, there is assumed a case where an unknown diffusing reflective surface S and a plurality of illuminations whose brightness and positions are known (in this example, two illuminations: a first illumination section L1 and a second illumination section L2) are present. For example, as shown in FIG. 13B, when irradiation is performed with light from the first illumination section L1, diffusing reflective light on the surface of the diffusing reflective surface S is decided only by: (1) brightness of the illumination (known); (2) an orientation of the illumination (known); (3) an orientation of the surface of the workpiece WK (normal vector n); and (4) a parameter of an albedo of the surface of the workpiece WK.

Figure 13C:
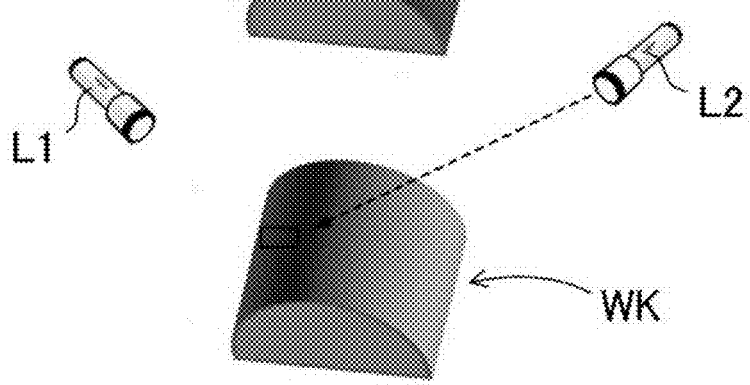
FIG. 13C is a view showing a state where light has been applied from L2.
Figure 13D:
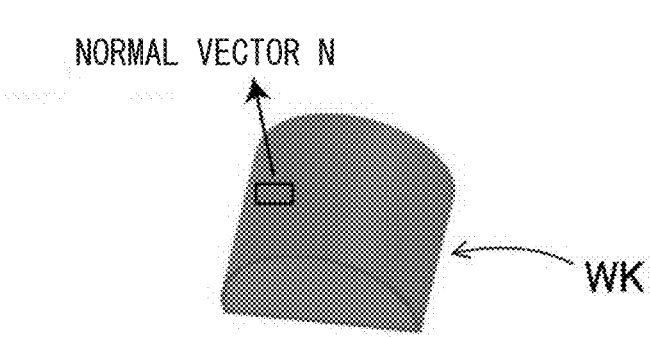
FIG. 13D is a view for explaining that an orientation of the surface is estimated from combination of an irradiation direction and brightness of reflective light, each for explaining a basic principle of a photometric stereo method.

Therefore, as shown in FIG. 13B and FIG. 13C, each of partial illumination images, obtained from diffusing reflective light at the time of projection of illumination light from a plurality of different illumination directions, specifically three or more illumination directions, is captured by the imaging section. Then, as shown in FIG. 13D, three or more partial illumination images are employed as input images, thereby allowing calculation of: (3) an orientation of the surface of the workpiece WK (normal vector n); and (4) an albedo of the surface of the workpiece WK, which are unknown, from the following relational expression.

$$I = \rho L S n$$

where $\rho$ is an albedo, L is brightness of the illumination, S is a matrix in the illumination direction, n is a normal vector of the surface, and I is a tone value of the image.

From the above expression, when the number of illumination sections is three, the following expression is given.

$$\begin{pmatrix} I_1 \\ I_2 \\ I_3 \end{pmatrix} = \rho L \begin{pmatrix} s_{11} & s_{12} & s_{13} \\ s_{21} & s_{22} & s_{23} \\ s_{31} & s_{32} & s_{33} \end{pmatrix} \begin{pmatrix} n_x \\ n_y \\ n_z \end{pmatrix} \quad \text{[Mathematical Expression 1]}$$

Further, when the number of illumination sections is four, the following expression is given.

$$\begin{pmatrix} I_1 \\ I_2 \\ I_3 \\ I_4 \end{pmatrix} = \rho L \begin{pmatrix} s_{11} & s_{12} & s_{13} \\ s_{21} & s_{22} & s_{23} \\ s_{31} & s_{32} & s_{33} \\ s_{41} & s_{42} & s_{43} \end{pmatrix} \begin{pmatrix} n_x \\ n_y \\ n_z \end{pmatrix}$$ [Mathematical Expression 2]

(Normal vector n)

From the above expression, the normal vector n can be expressed by the following expression.

$$n = 1/\rho L \cdot S^+ I$$

In the above expression, when "$S^+$: a square matrix", "a normal inverse matrix $S^+$: an inverse matrix of a longitudinal matrix" is found by Moore-Penrose pseudo-inverse matrix $S^+ = (S^t S)^{-1} S^t$.

(Albedo)

Further, the albedo ρ can be expressed by the following expression:

$$\rho = |I|/|LSn|$$

(2-2. Contour Extraction Image)

Next, a description will be given of a method for generating an inclination image by the photometric stereo method and obtaining information of the surface of the workpiece, such as a flaw and a contour, from the obtained inclination image.

(Inclination Image)

First, a method for generating the inclination image will be described. When it is assumed that the curved surface of the workpiece is S, the inclination image is given by the following expression:

X-direction: $\delta s/\delta x$, Y-direction: $\delta s/\delta y$

Figure 14A:
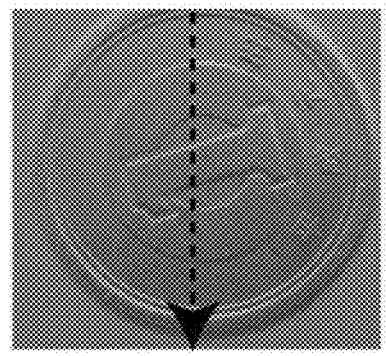
FIG. 14A is a view showing one example of an inclination image differentiated in a vertical direction.
Figure 14B:
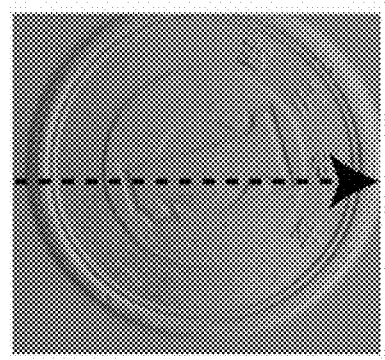
FIG. 14B is a view showing one example of an inclination image differentiated in a horizontal direction.

Here, as examples of the inclination image, FIGS. 14A and 14B show examples of using a one-yen coin as the workpiece. FIG. 14A is a Y-coordinate component image in a normal direction, and FIG. 14B is an X-coordinate component image in a normal direction. Here, by use of partial illumination images captured from four illumination directions, an inclination image shown in FIG. 14A is obtained by performing differentiation in the Y-direction (a vertical direction in the drawing), and an inclination image shown in FIG. 14B is obtained by performing differentiation in the X-direction (a horizontal direction in the drawing).

Here, since a flaw, a contour and the like are places where the inclination of the surface of the work piece changes, the inclination images are differentiated in the respective directions. The secondary inclination image is given by the following expression:

X-direction: $\delta^2 s/\delta x^2$, Y-direction: $\delta^2 s/\delta y^2$ (Contour Extraction Image)

Thus, the portions $\delta^2 s/\delta x^2$, $\delta^2 s/\delta y^2$ of the inclination images in the X-direction and the Y-direction are synthesized to generate a contour extraction image including information of a contour and a flaw of the workpiece. A contour extraction image E is given by the following expression.

$$E = \delta^2 s/\delta x^2 + \delta^2 s/\delta y^2$$

Figure 14C:
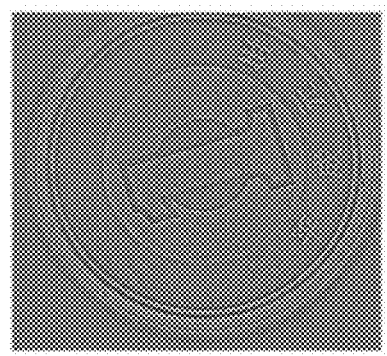
FIG. 14C is a view showing one example of a contour extraction image, each for explaining a method for generating a contour extraction image.

In the above expression, E represents contour information, and S represents the curved surface of the workpiece. FIG. 14C shows an example of the contour extraction image computed from FIGS. 14A and 14B. In the contour extraction image, a height is expressed by gradation (luminance) of the image such that a high portion is colored in white and a low portion is colored in black.

(Differentiation Synthesis Method)

Examples of a differentiation synthesis method that is performed in generating the contour extraction image include: (1) simple addition; (2) multiple resolution; and (3) square sum.

(1. Simple Addition)

Here, "(1) simple addition" is a sum of differentials of X/Y-inclination images at each pixel.

(2: Double Resolution)

Further, "(2) multi-resolution" is obtained by creating a plurality of reduced inclination images, obtained by reducing the inclination image at different reduction ratios, and finding intensity of a contour in each of the reduced inclination images by the method of (1). The reduction ratios are, for example, 1/1, 1/2, 1/4, 1/8, 1/16, 1/32 and the like. The plurality of reduced contour images as thus obtained are subjected to predetermined weighting and enlargement processing, and an image obtained by adding all the enlarged reduced contour images is regarded as a contour extraction image. Here, when the weighting is changed, a flaw, a contour and the like each having an arbitrary thickness can be extracted.

(3. Square Sum)

Further, in "(3) square sum", a contour extraction image is created in which a sum of a square of differentials of the X/Y-inclination images is regarded as intensity of a contour. It is to be noted that "(2) multi-resolution" is adopted in the present embodiment.

A size used for flaw determination varies depending on the user's use. For example, a depression over ten pixels may be determined as a flaw, or a depression over 100 pixels may be determined as a flaw. Further, only a steep edge may be to be extracted as an edge.

When the number of pixels of the inclination image is large, it is regarded as a large flaw in the processing. Therefore, when a large flaw is to be extracted, an inclination image is reduced, intensity of a contour is found by the method of (1), and then the image is enlarged. On the other hand, when a small flaw is to be extracted, differential synthesis may be performed by the method of (1) without performing weighting.

That is, in the weighting, a previously decided weighting set is prepared at the time of synthesis, and reduced inclination images of all the kinds described above are created. Then, when a large flaw is to be seen, a result from the more reduced image is weighted, and when a small flaw is to be seen, a result from the less reduced image is weighted.

Here, the contour extraction image is obtained by adding all the reduced contour images having been enlarged. Since a flaw is normally detected over a plurality of frequencies, when the frequency is limited to one frequency, for example, only a flaw detected at that limited frequency is extracted and hence the image blurs as a whole.

(Characteristic Size)

The foregoing weighting set is formed such that, for example, a parameter named a "characteristic size" is provided, the thinnest flaw can be detected when this value is 1, and a larger flaw is detected as this value continues to be increased. When the characteristic size continues to be increased and the image comes into a state where a larger flaw is easy to detect, the roughness of the surface of the workpiece becomes more apparent. Therefore, a predetermined threshold may be provided for the characteristic size, and a case where the characteristic size is equal to or larger than the threshold is a roughness mode, which may then be used separately from a contour extraction mode, depending on the characteristic size of the contour extraction image.

Next, a method for calculating $\delta^2 s/\delta x^2$ and $\delta^2 s/\delta y^2$ will be described. Examples of this calculation method include: (1) forward difference; and (2) central difference.

(1. Forward Difference)

In the forward difference, an inclination image Gh in the horizontal direction and an inclination image Gv in the vertical direction are regarded as input, and a pixel G(x,y) at coordinates (x,y) of a contour image E is calculated by the following expression:

$$E(x,y)=Gh(x-1,y)-Gh(x,y)+Gv(x,y-1)-Gv(x,y)$$

Figure 15A:
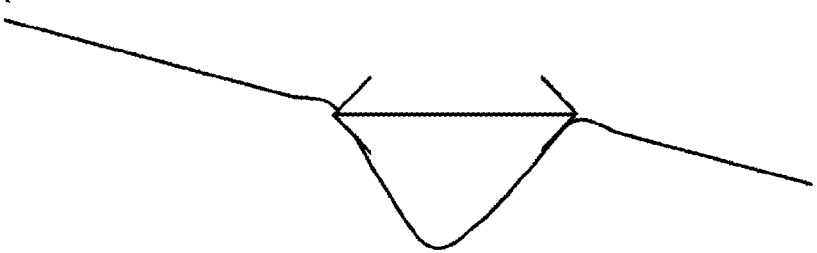
FIG. 15A is a view showing surface information.
Figure 15B:
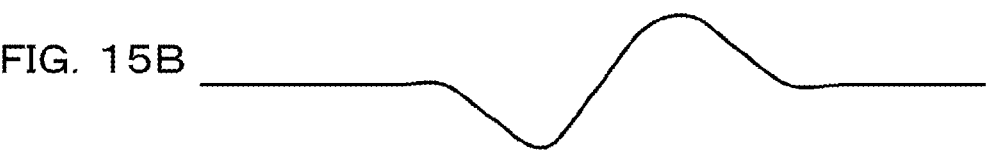
FIG. 15B is a diagram showing an inclination image.
Figure 15C:
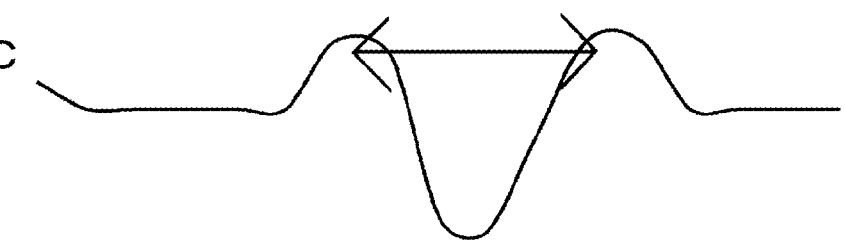
FIG. 15C is a view showing a forward difference.
Figure 15D:
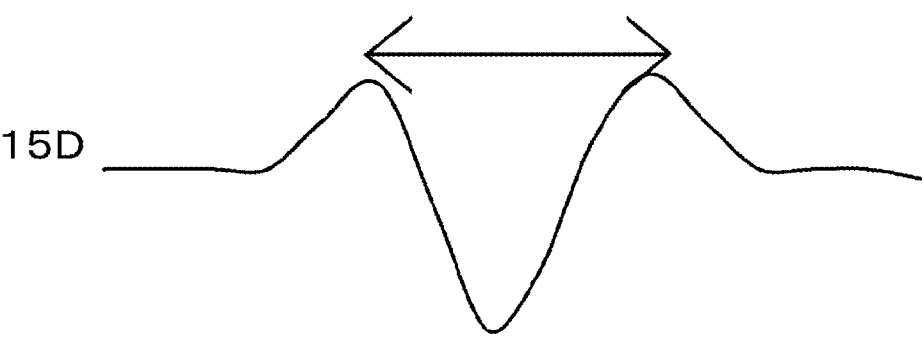
FIG. 15D is a view showing a central difference, each for explaining a method for calculating $\delta^2 s/\delta x^2$ and $\delta^2 s/\delta y^2$.

Here, FIGS. 15A to 15D show information of a flaw that appears in a contour image as schematic profiles. In these drawings, FIG. 15A shows a profile of surface information of the workpiece, FIG. 15B shows a profile of an inclination image, FIG. 15C shows a profile of a contour image by means of a forward difference, and FIG. 15D shows a profile of the contour image by a central difference. As shown in FIGS. 15A and 15C, "(1) forward difference" has an advantage in that a flaw in units of one pixel can be clearly seen, but has a disadvantage in that an image displaced by 0.5 pixels from the original image is obtained.

(2. Central Difference)

Next, a method for calculating $\delta^2 s/\delta x^2$ and $\delta^2 s/\delta y^2$ by means of the central difference will be described. An inclination image Gh in the horizontal direction and an inclination image Gv in the vertical direction are regarded as input, and a pixel G(x,y) at coordinates (x,y) of a contour image E is calculated by the following expression:

$$E(x,y)=Gh(x-1,y)-Gh(x+1,y)+Gv(x,y-1)-Gv(x,y+1)$$

As shown in FIGS. 15A and 15D, "(2) central difference" has an advantage in that coordinates are not displaced from the original image, but has a disadvantage in that a result slightly blurs.

(2-3. Texture Extraction Image)

Next, a description will be given of a method for removing the surface state of the workpiece from an inclination image obtained by the photometric stereo method, to obtain a texture extraction image preferable for detection of a character, and the like. First, texture information is calculated from the albedo ρ of the surface of the workpiece. The albedo ρ is given by the following expression.

$$\rho = |I|/|LSn|$$

where ρ is an albedo, L is brightness of the illumination, S is a matrix in the illumination direction, n is a normal vector of the surface, and I is a tone value of the image.

It is to be noted that, while it is possible to find one texture extraction image (albedo) by the expression: $\rho=|I|/|LSn|$, it is also possible to find N texture extraction images (albedos) from a normal vector obtained by this expression and N input images (partial illumination images) and synthesize the texture extraction images, so as to find one texture extraction image (albedo). Examples of a specific synthesis method include an average method and a halation removing method.

Figure 16A:
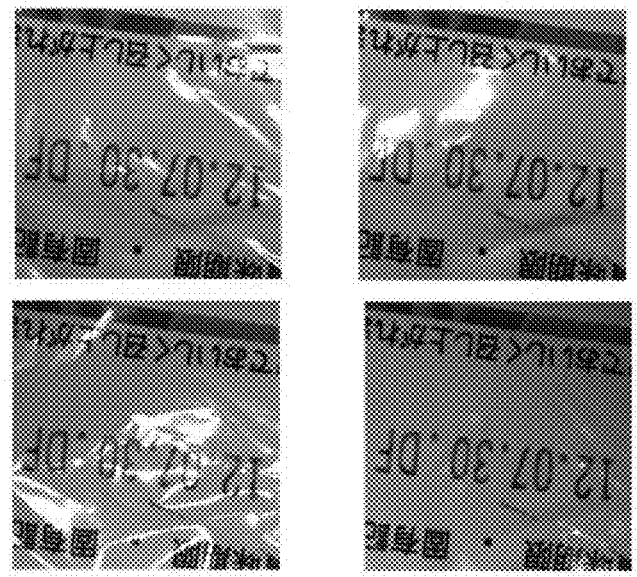
FIG. 16A is a view showing a source image.
Figure 16B:
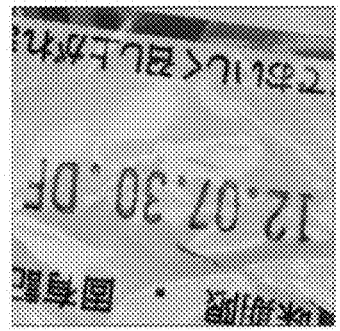
FIG. 16B is a view showing an image subjected to processing by an average method.
Figure 16C:
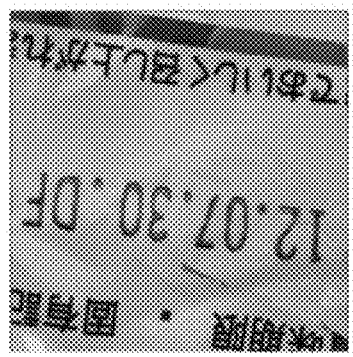
FIG. 16C is a view showing an image subjected to processing by a halation removing method, each for explaining a method for generating a texture extraction image.

FIGS. 16A to 16C show examples of the texture extraction image. In these drawings, FIG. 16A shows four texture extraction images as input images, FIG. 16B shows a texture extraction image obtained by applying the average method to these images, and FIG. 16C shows a texture extraction image obtained by applying the halation removing method to these images.

(1: Average Method)

The average method is a method where at each pixel, an average value of N albedos ρ is regarded as a pixel value of that pixel. As shown in FIG. 16B, although the shadow is entirely erased, the shadow in a portion where halation has occurred in the input image cannot be erased by the photometric stereo method, and hence an image where an influence of the halation remains is obtained. That is, in the four input images (partial illumination images) of FIG. 16A, white places are places where halation has occurred. When averaging is performed by the average method, as shown in FIG. 16B, the roughness is removed to a certain extent and the image becomes easier to read, but the roughness slightly remains on a base.

(2: Halation Removing Method)

The expression: $\rho=|I|/|LSn|$ itself exceeds its application range due to a limitation on a dynamic range of the camera as the imaging section and the diversity of reflectivity of the surface of the workpiece, and hence ρ includes an error. In order to correct this error, the halation removing method can be used.

Since a place where halation occurs is decided by a position of illumination, it is considered that basically, halation does not occur in the same place in the four partial illumination images. Specifically, although halation may occur over two places between two directions, it can be said that halation basically does not occur in the same place unless two illuminations are used.

In the halation removing method, at the time of synthesizing a illumination-direction-specific texture extraction image calculated from N partial illumination images, considering that there is much halation in a partial illumination image with the largest pixel value at each pixel or in partial illumination images with the largest to N-th largest pixel values, those are removed and the synthesis is then performed.

Specifically, when each of pixels of the four illumination-direction-specific texture extraction images in the present embodiment is synthesized with the third largest pixel value (e.g. albedo value or luminance), an image as shown in FIG. 16C is obtained, and an influence of halation can be removed. It is to be noted that, when the fourth largest pixel value is adopted, a slightly dark image is obtained due to an influence of a shadow. On the contrary, when the second largest pixel value is adopted, the influence of halation slightly remains.

Further, in the case of the illumination sections being in the eight directions, the fifth largest pixel value is adopted on the assumption that the influence of halation is not exerted on the fifth largest pixel value or the following pixel value. According to a test performed by the inventor, it has actually been confirmed that the best image is obtained when the fifth largest pixel value is adopted. Further, it has also been proved that the influence of the shadow is exerted when the sixth largest pixel value or the following pixel value is adopted.

It is to be noted that the synthesis method and the averaging are not restricted to these, and a variety of methods can be used. For example, the foregoing halation removing method and average method may be combined, to sort albedo values and adopt values in a specific orders from the top. For example, the third and fourth values may be averaged.

(Characteristic Size)

Next, a detail of the setting will be described. As described above, at the time of creating the contour extraction image, the characteristic size can be set. By setting the characteristic size to not smaller than a predetermined value, a contour extraction image suitable for OCR can be obtained.

(3-2. Gain)

At the time of creating a contour extraction image or a texture extraction image, in the process of generating each of these images, it is possible to multiple a pixel value of the original image by a gain.

The gain at the time of creating a contour extraction image refers to a constant at the time of dispersing a pixel value calculated by calculation processing to a gradation of 0 to 255. For example, when a flaw, a contour or the like is so shallow that it is difficult to grasp the flaw, the contour or the like, a change in gradation of the pixel value increases by increasing this gain value, and hence the flaw, the contour or the like becomes easy to grasp.

Further, the flaw, the contour or the like becomes easy to grasp by performing adjustment such that, when the pixel value calculated by the calculation processing exceeds the range of 0 to 255, it is made to be within that range, and when the pixel value is smaller than the range of 0 to 255, it is extended into that range.

In the foregoing halation removing method, since albedo values are sorted and, for example, the third value from the top is adopted, the brightness of the generated image cannot be expected. Accordingly, as a result of removal of regular reflection, the image may become dark contrary to the expectation. Therefore, in order to adjust the brightness, the pixel value is multiplied by a predetermined gain at the time of creating a texture extraction image.

It is to be noted that, also at the time of calculating an inclination image, adjustment can be performed by means of a gain such that the pixel value is made to be within the range of 0 to 255.

(3-3. Noise Removing Filter)

At the time of creating an inclination image or the like, calculation is to be performed by a set of simultaneous equations by use of a plurality of images, but in practice, differential calculation is performed. Here, noise exists in image data which is obtained by imaging by the imaging section, when the image data is raw data. Therefore, a noise component may be emphasized and a contour may become rough at the time of creating an inclination image. In order to reduce such noise, a noise removing filter such as a guided filter is used. A general low-pass filter may hide or remove not only noise but information of a flaw. On the contrary, a guided filter can remove noise while keeping an edge at the time of finding the inclination image, which is preferable.

(3-4. Angle-Noise Reduction)

Figure 17:
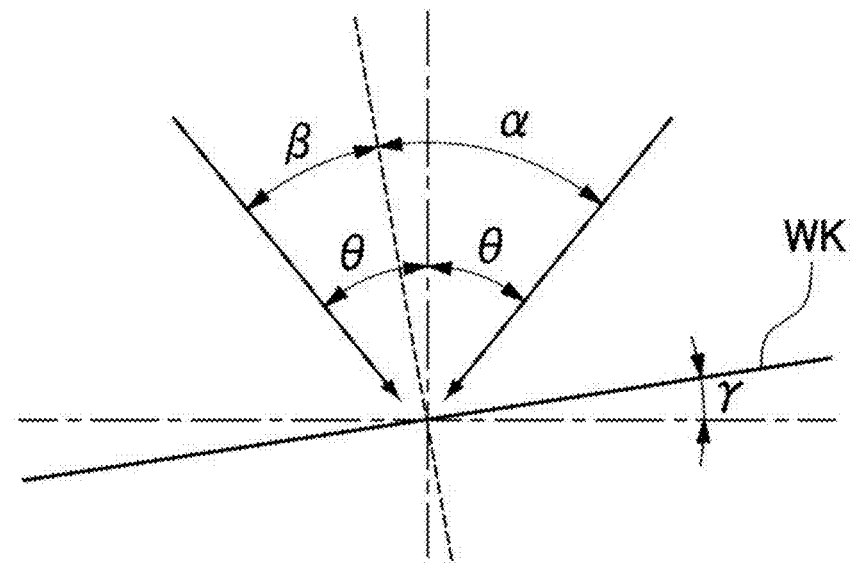
FIG. 17 is a diagram for use in explaining angle-noise reduction.

Next, a principle of angle-noise reduction will be described with reference to a schematic view of FIG. 17. As shown in this drawing, there are two illuminations whose incident angles are $\alpha$ and $\beta$. When the workpiece WK is assumed to be formed of the diffusing reflective surface and setting is performed such that the inclination of the workpiece WK with respect to the reference plane is $\gamma$, an angle between a line perpendicular to the reference plane and an incident is $\theta$, the brightness of reflective light from the illumination $\alpha$ is $I_\alpha$ and the brightness of reflective light from the illumination $\beta$ is $I_\beta$, $\gamma$ is given by the following expression:

$$\gamma = \arctan(A \cdot |I_\beta - I_\alpha|/|I_\beta + I_\alpha|), A = \cot\theta$$

Angle-noise reduction is to forcibly make the inclination $\gamma$ be 0 when $|I_\beta + I_\alpha|$ is small to a certain extent.

When it is assumed that both $I_\beta$ and $I_\alpha$ are extremely dark and $I_\beta = 2$ and $I_\alpha = 1$, for example, $|I_\beta - I_\alpha|/|I_\beta + I_\alpha|$ becomes a value as large as ⅓. On the other hand when it is assumed that both $I_\beta$ and $I_\alpha$ are bright and $I_\beta = 300$ and $I_\alpha = 200$, for example, $|I_\beta - I_\alpha|/|I_\beta + I_\alpha|$ becomes a value as small as ⅕. $I_\beta = 2$ and $I_\alpha = 1$ greatly affects inclination although there is simply a possibility of noise. Thus, in order to reduce an influence of such noise, the angle-noise reduction is applied to allow setting of a threshold of $|I_\beta + I_\alpha|$ for forcibly making the inclination be 0.

(Structure of Separate Model of Illumination Section and Imaging Section)

In the image inspection using the photometric stereo method, corresponding positions of the illumination section and the imaging section are required to be strictly defined in advance. For this reason, in the conventional image inspection apparatus, the illumination section and the imaging section have been integrally configured. In other words, since the photometric stereo method is a measurement method for performing accurate three-dimensional measurement after strictly positioning the relative positions of the imaging section and the illumination section, the degree of freedom in installation positions has not been originally provided at the time of installing the illumination section and the imaging section. However, in the configuration where the illumination section and the imaging section are fixed in advance, the imaging illumination unit with the illumination section and the imaging section integrated necessarily becomes large in size, to worsen the handling thereof.

Figure 18:
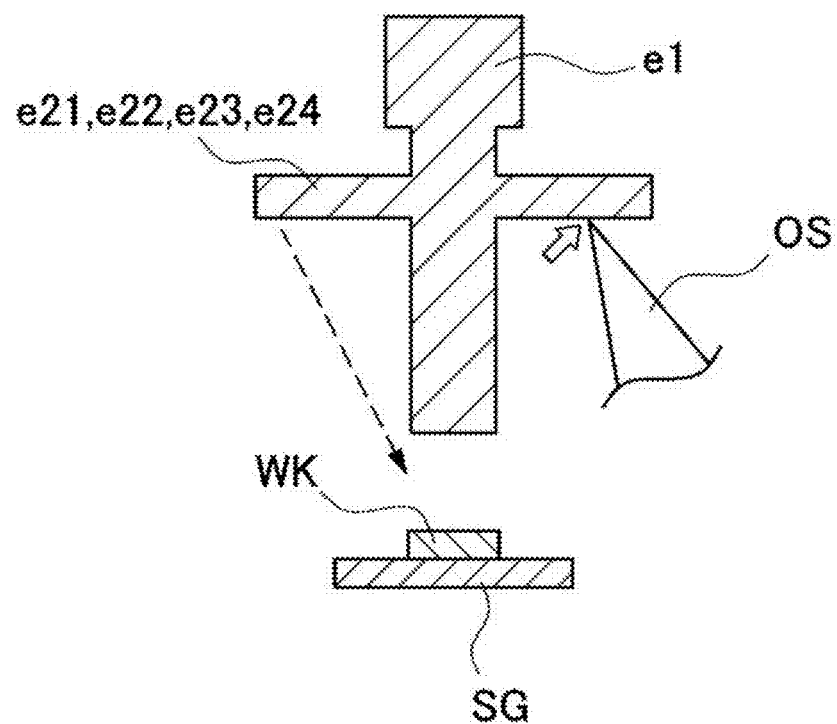
FIG. 18 is a schematic cross section showing a state where, in the case of an illumination-camera integrated model, it interferes with an obstacle.
Figure 19:
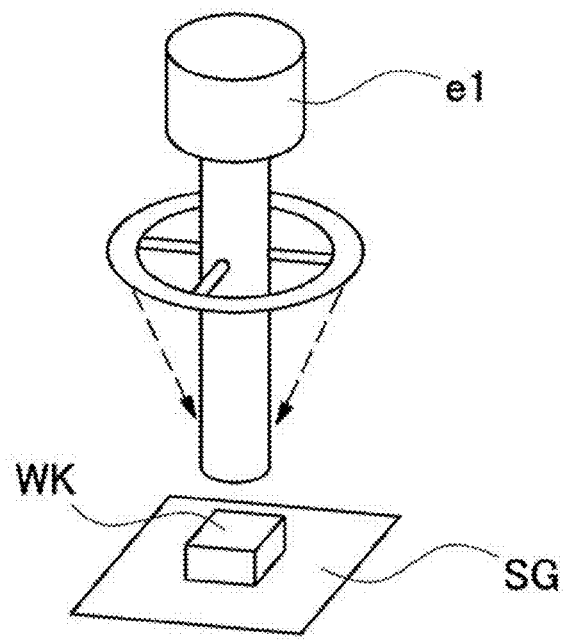
FIG. 19 is a schematic view showing a state where the camera blocks part of illumination light.

For example, when an obstacle exists in an inspection position, there occurs a situation where the obstacle interferes with the imaging illumination unit to prevent installation. In particular, a lens mounted in a camera as one form of the imaging section may have a large size, such as a line camera, a zoom lens or a large-sized macro-lens. When the imaging section becomes longer as in the case of a large-sized lens being mounted in the imaging section, it increases the risk of interference between an obstacle OS existing around the workpiece WK and a camera e1 or light sources e21 to e24 for illumination arranged around the camera, as shown in FIG. 18. Further, when the camera e1 as the imaging section becomes long, it is considered that illumination light is partially blocked by the camera e1 or part of the lens as shown in FIG. 19 to disrupt illumination by, for example, casting a shadow on the workpiece WK. When the imaging illumination unit is arranged to a position where the imaging illumination unit and the obstacle do not interfere with each other in order to avoid such a situation as above, a distance between the illumination section and the workpiece (Light Working Distance: LWD) becomes long, whereby a light amount of the illumination light decreases to lead to deterioration in inspection accuracy.

Figure 20:
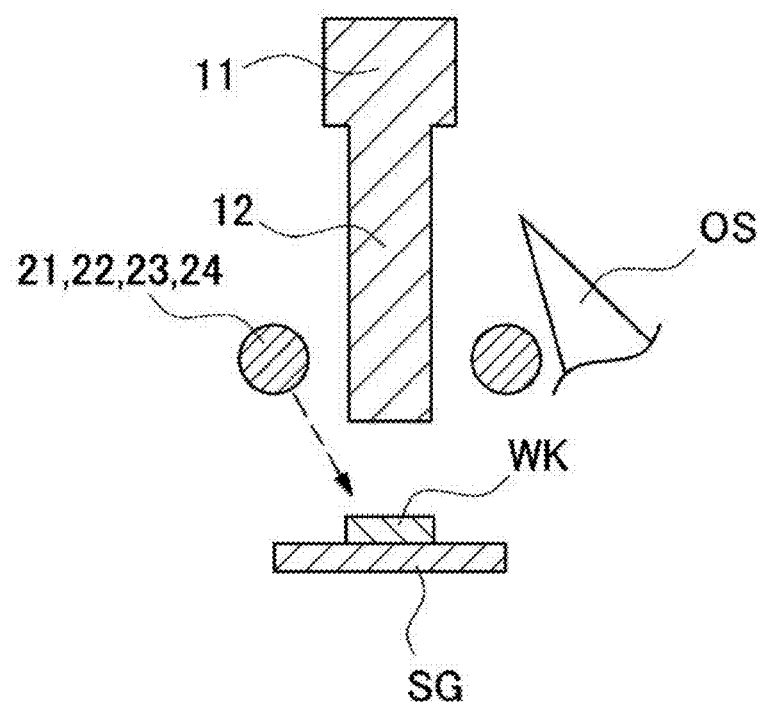
FIG. 20 is a schematic sectional view showing a configuration of an illumination-camera separate model.

In contrast, if the imaging section and the illumination section can be provided separately, it is easy to arrange them in positions where they do not interfere with the obstacle. For example, even when the obstacle OS shown in FIG. 18 exists, the illumination sections 21 to 24 can be installed in positions where the obstacle does not interfere, as shown in FIG. 20, by separating the illumination sections 21 to 24 from the imaging section 11. Similarly, even in the case of mounting a large-sized lens in the imaging section, adjustment can be performed so as to avoid physical interference of the lens 12 to the illumination sections 21 to 24. By forming a separate model of the illumination sections 21 to 24 and the imaging section 11 as thus described, it is possible to adjust them to be in positions where they do not interfere with the obstacle, and the like, so as to enhance the degree of freedom in installation and inspect the workpiece WK in a variety of environments.

Further, it is also possible to adjust an attachment position of the illumination section and the like such that the imaging section does not block the illumination light. Similarly, it is also possible to adjust an arrangement position of the illumination section so as to suppress influences of halation and a shadow. Especially in the photometric stereo method, since it is assumed that the surface of the workpiece is the diffusing reflective surface, generally, the normal vector of the surface of an inclination image obtained by the photometric stereo method is displaced from the normal vector of an actual surface of the workpiece. Therefore, a countermeasure such as second-order differentiation has been performed. In addition to such a countermeasure, adjustment of the attitude of the illumination section is performed so as to avoid the halation at the time of installation of the illumination section, which can reduce such displacement. Further, similarly to the mirror surface, such large roughness which causes a change in brightness is adversely influenced by halation. For example, in the case of the workpiece having a cylindrical shape, specular reflection occurs when irradiation is performed with illumination light, but when roughness exists here, it comes to be not a little influenced by the specular reflection. Accordingly, by giving the degree of freedom to the installation position and the angle of illumination light, an advantage can be obtained in which adjustment is performed in advance so as to reduce such specular reflection and further improve the inspection accuracy.

Moreover, in the photometric stereo method, an influence of a shadow is required to be considered. In the photometric stereo method, detection of reflective light is essential for calculating a normal vector from reflective light of illumination. However, in a case where the workpiece has a complex shape and is apt to have a shadow, when the illumination section is installed in the vicinity of this workpiece, appropriate reflective light is not obtained from a place where light is not reached, which may disrupt calculation of the normal vector. Even in such a case, the illumination sections 21 to 24 can be installed in optimum positions at optimum angles by separating the illumination sections 21 to 24 and the imaging section 11 from each other, so as to suppress such an influence.

Additionally, a height of illumination light can be changed by separating the illumination section from the imaging section. As a result, it is possible to perform inspection where the distance LWD (Light Working Distance) between the workpiece WK and illumination is made small or, on the contrary, large so as to select appropriate arrangement in accordance with the inspection use.

(1: Case of Making LWD Short)

Figure 21A:
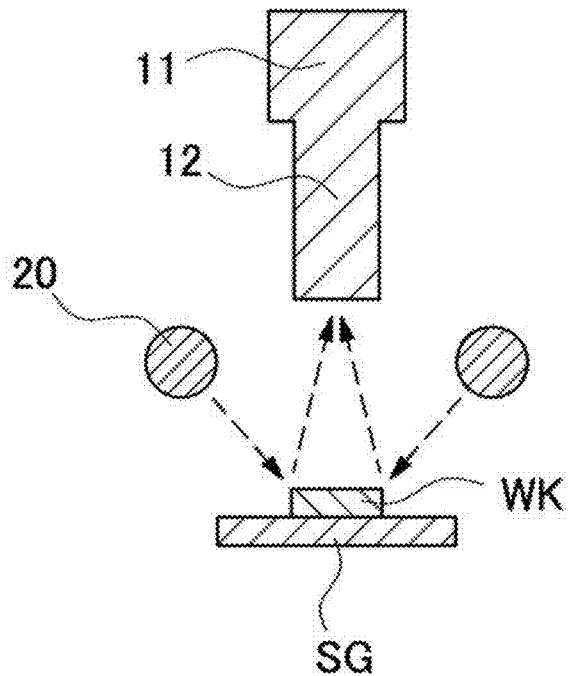
FIG. 21A is a view showing a case where an LWD is made short.

When the LWD is made short, as shown in FIG. 21A, light from each of the illumination sections 21 to 24 is much applied from a lateral direction. Since halation generally occurs when an incident angle and a reflection angle are the same, by bringing the illumination sections 21 to 24 and the workpiece WK close to each other to make the LWD short, a position where halation occurs can be made to be in the vicinity of the outside of the workpiece WK. In other words, by intentionally making halation apt to occur outside the workpiece WK, halation in the vicinity of the surface of the workpiece WK can be suppressed. This can increase an effective visual field of the workpiece WK.

Further, when the LWD is short, illumination is performed at a low angle. For example, even when there is roughness on the surface of the workpiece where light of direct illumination from above is diffused and recognition is difficult, by irradiating the roughness from the oblique side surface, it is possible to greatly change a contrast even by a small change in inclination, so as to facilitate grasping a change in shallow roughness. By emphasizing a contrast at a low angle, it is possible to obtain an advantage that an inclination image and a contour extraction image can be made clear in the photometric stereo method.

On the other hand, a disadvantage in the case of making the LWD short is that a shadow is apt to occur due to irradiation with illumination light at a low angle, causing reduction in effective visual field and making the photometric stereo processing difficult. Further, since the illumination sections 21 to 24 and the workpiece WK are apt to interfere with each other, making the LWD short is limitedly used for the workpiece WK with a large height.

(2: Case of Making LWD Long)

Figure 21B:
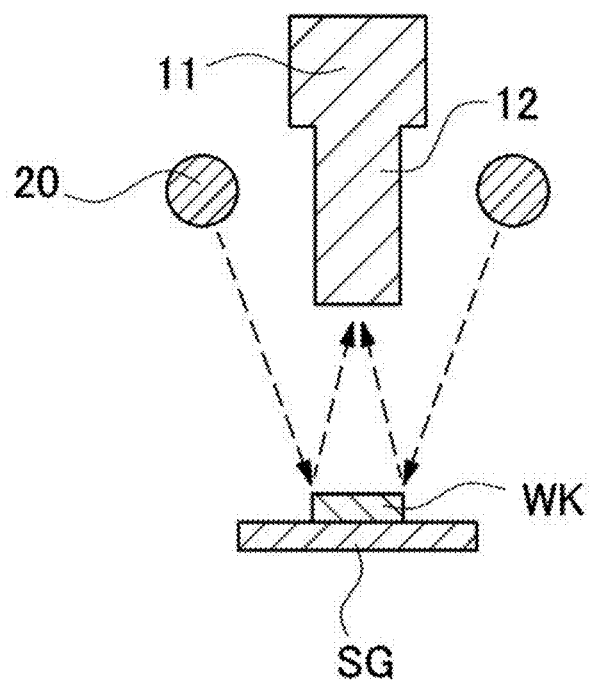
FIG. 21B is a view showing a case where the LWD is made long, each for explaining an advantage of the illumination-camera separate model.

On the contrary, when the LWD is made long, as shown in FIG. 21B, irradiation is performed with much illumination light from the illumination sections 21 to 24 from above. This makes a shadow hardly occur, thus reducing an invisible region, to improve the accuracy in photometric stereo processing. Further, since the illumination sections 21 to 24 and the workpiece WK hardly interfere with each other, making the LWD long can be used preferably with respect to the workpiece WK with a large height.

On the other hand, since the position where halation occurs is inside the workpiece WK, the effective visual field may be reduced. Further, the case of the LWD being long corresponds to the case of the LWD being long in multi-angle illumination, and a contrast is hardly made, whereby a change in shallow roughness of the surface of the workpiece may be less likely to be grasped. However, when the LWD is long, it is possible by multi-angle illumination to create a uniform imaging state with little reflection and uneven illuminance of the illumination sections 21 to 24, so as to obtain an image clearly capturing the surface state of the workpiece WK itself.

As thus described, by separating the imaging section and the illumination section, it is possible to obtain an advantage that inspection is adaptable to a variety of purposes and uses and the degree of freedom in arrangement can be enhanced. Especially a normal vector calculated by the normal vector calculating section has such dependency that intensity of the normal vector changes in accordance with a change in relative distance between the imaging section and the illumination section in an optical axis direction of the imaging section. That is, when a light amount of the illumination section is the same, there is a tendency that, the shorter the relative distance, the larger the intensity of the normal vector, and the longer the distance, the smaller the intensity of the normal vector. The larger the intensity of the normal vector, the more clearly the inclination (roughness shape) of the surface of the workpiece appears, and hence the accuracy in the obtained inspection image also improves. Therefore in the conventional photometric stereo method, for improving the accuracy, the relative position of the imaging section and the illumination section has been strictly defined in advance so as to obtain large intensity of the normal vector. That is, the intensity of the obtained normal vector has been enhanced by fixing the imaging section and the illumination section in advance.

In visual inspection of a flaw on the surface of the workpiece or OCR, high accuracy is not necessarily required, and for example, it may often be sufficient when detection can be performed with the accuracy that can determine the presence or absence of the flaw or perform OCR on a number or a character. In such a use, enhancing the degree of freedom in installation of the camera and the light is more advantageous for the user than enhancing the accuracy. Hence in the present embodiment, enhancing intensity of a normal vector is not in focus, but rather than that, reduction in intensity of the normal vector is permitted and a level on which the accuracy necessary for visual inspection is sufficiently obtained is kept. In compensation for this, it is made possible to install a light and a camera which are released from constraints of fixation of the illumination section and the imaging section and which have a higher degree of freedom, leading to a success in improvement in convenience of the user.

In the case of constituting the illumination section and the imaging section as separate bodies and performing image inspection by the photometric stereo method, it is necessary to precisely set a relative positional relation between the illumination section and the imaging section. If there is a significant difference between a set illumination direction and an actual illumination direction, the inspection accuracy may deteriorate or an erroneous result may be outputted. It can be considered that, for example, when the user makes a mistake in connection of a large number of illumination sections or installs them with azimuths displaced as a whole at the time of installing the imaging section and the illumination section, accurate inspection cannot be performed.

Figure 22:
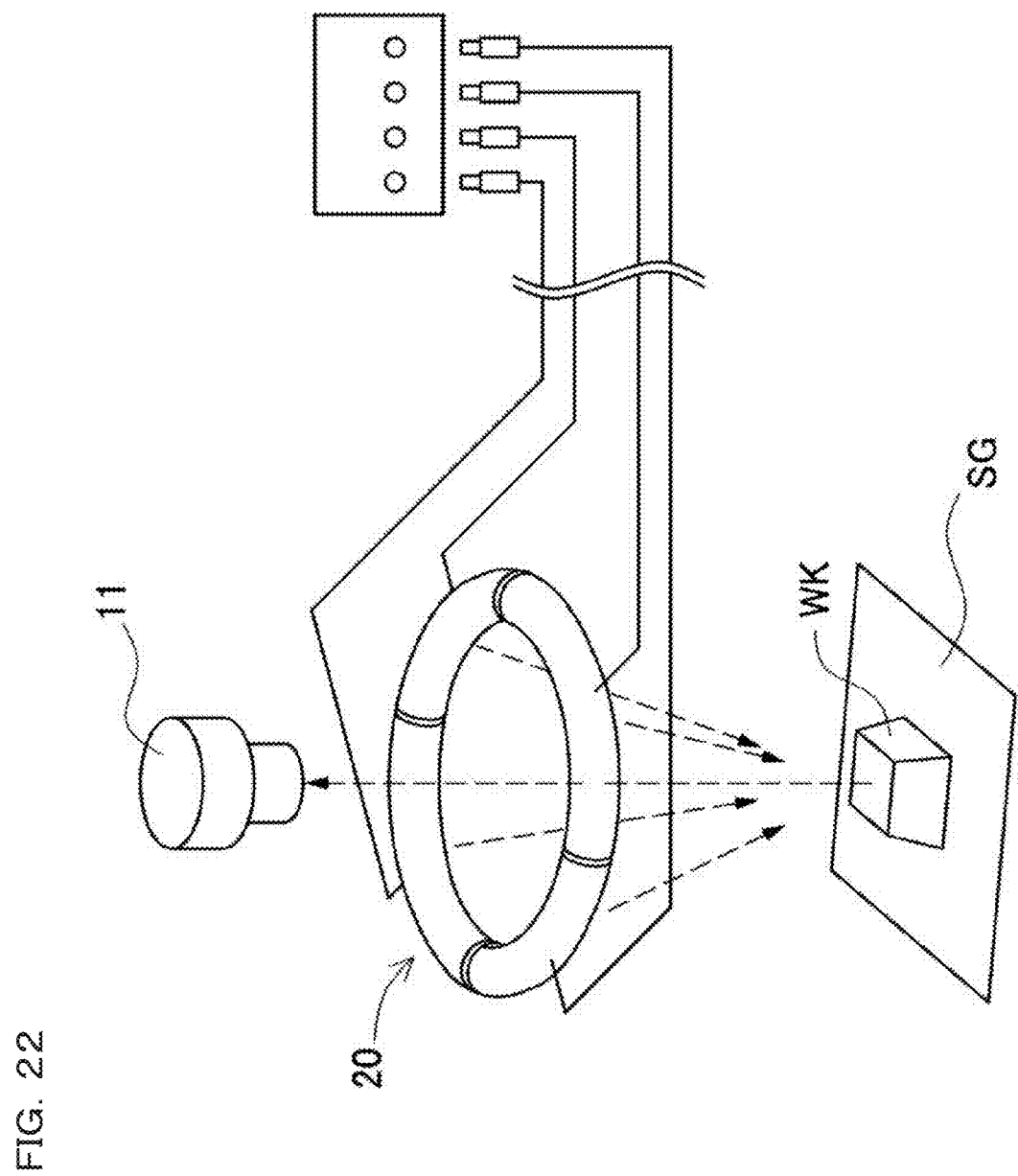
FIG. 22 is a schematic view showing a state where a ring-like illumination is arranged.

For example, there is considered a case where, as shown in FIG. 22, the imaging section is arranged above the workpiece on a vertical line where the workpiece is arranged, and further, the illumination sections are respectively arranged in the north, south, east and west so as to surround the workpiece. In such arrangement, in the case of acquiring a height shape of the workpiece by use of the photometric stereo method, when the shapes of each of the illumination sections and the illumination cable are common, mix-up of connection or arrangement can occur. Specifically, it is configured such that a predetermined illumination cable is connected to an illumination connector provided in the illumination dividing unit, the shape of each illumination cable is generally made common, and similarly, the shape of each illumination connector is common. Accordingly, it can happen that the illumination cable is connected to a wrong illumination connector. In particular, the mix-up is apt to occur when a long illumination cable is drawn. Further, it is can be considered that, when the illumination section is installed above the periphery of the workpiece, the illumination sections with the same shape may be mixed up and fixed.

Figure 23:
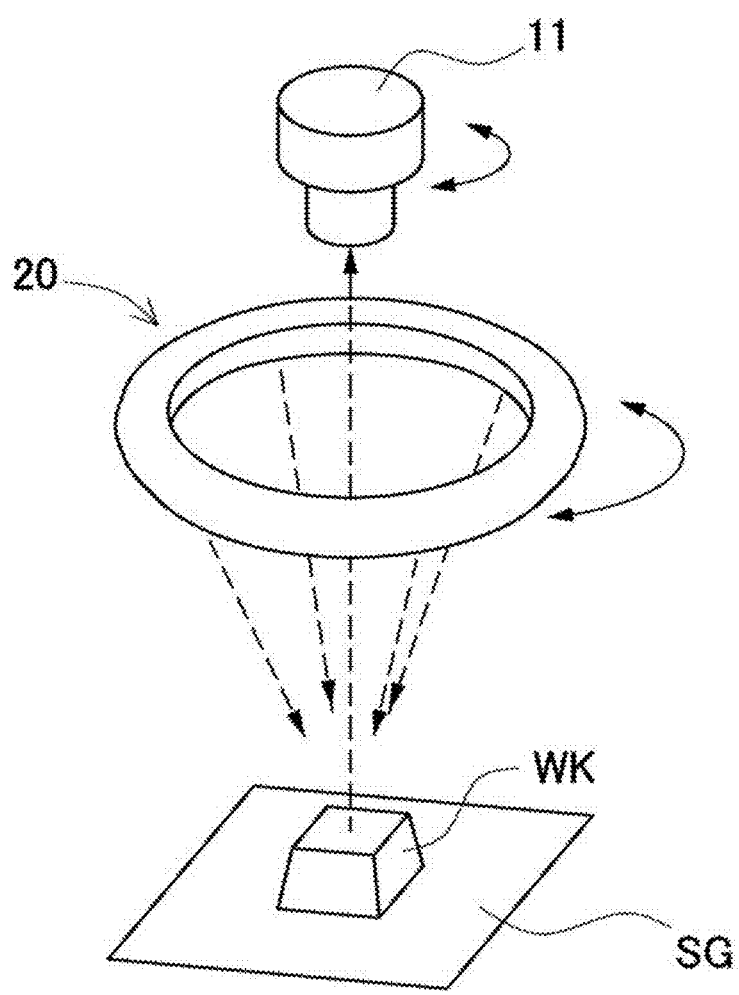
FIG. 23 is a schematic view showing a state where rotational positions of the ring-like illumination and the camera are matched with each other.

As shown in FIG. 23, also in the example of arranging a ring-like illumination section, it is necessary to match a direction of the illumination light with a rotational angle of the imaging section. In this case, when the imaging section and the illumination section have a point-symmetric shape such as a cylindrical shape or an annular shape, rotational angles thereof are difficult to determine, and alignment is not easy. As a result, the rotational position may be displaced from an intended position. In particular, there has been a fact that the user hardly notices the installation error of the illumination section because a characteristic amount such as a shape of the surface of the workpiece can be detected to a certain extent even when the rotational angle, the arranged position or the like is slightly erroneously set. Further, in the case of complete mix-up of the illumination sections, the setting error is relatively noticeable, but in the case of a setting error like small displacement of a rotational angle, the user hardly notices the error, leading to deterioration in accuracy, which has been problematic.

Accordingly, in the present embodiment, at the time of acquiring partial illumination images obtained by illumination from a plurality of different illumination directions by the photometric stereo method, there is set an installation auxiliary section for supporting correct setting at the time of installation such that the illumination direction and the turning-on order of the illumination section are set as intended. Specifically, in FIG. 1, at the time of connecting each of the illumination sections and the illumination controlling section, appropriate connection destinations are shown to the user along predetermined installation setting such that the illumination direction matches with the turning-on order. Alternatively, in order that an attitude (rotational position or rotational angle) of each of the illumination sections in a circumferential direction matches, a correct attitude is instructed to the user at the time of installing the illumination section. Hence it is possible to prevent an error at the time of installation, so as to accurately perform visual inspection of the workpiece by the photometric stereo method.

(Installation Setting)

Here, installation setting is setting in which, in order to correctly calculate a normal vector by the photometric stereo method, an installation position is defined in accordance with the number of illumination sections so that the workpiece can be irradiated with illumination light from predetermined illumination directions. For example, as shown in the plan view of FIG. 2, in the example of using four illumination sections, in order to arrange the four illumination sections of the first illumination section 21, the second illumination section 22, the third illumination section 23 and the fourth illumination section 24 around (to the north, south, east and west of) the workpiece, the installation setting includes installation position information for illumination that the first illumination section 21 is arranged in the north, the second illumination section 22 in the east, the third illumination section 23 in the south and the fourth illumination section 24 in the west. Further, the installation setting may include the turning-on order of the illumination sections and the imaging timing for the imaging section by the illumination controlling section.

(Installation Auxiliary Section)

Hereinafter, a specific example of the installation auxiliary section will be described. In the example shown in FIG. 1, connection destinations of the imaging section 11, the illumination sections 21 to 24 and the illumination dividing unit 75 are indicated by the installation auxiliary section so as to form an intended connection where the photometric stereo processing is appropriately performed, in other words, such that erroneous connection or arrangement are not performed. For example, installation written indicators each showing a specific direction or a rotational angle of arrangement of illumination are provided in connection portions, or connectors or terminals to be connected to each other are made to have commonality or correspondence by means of characters, symbols or other marks, shapes, colors or the like of installation written indicators, thereby to visually show arrangement positions, directions, rotational angles, connection destinations, or the like. In such a manner, by supporting a mutual connecting operation by the installation auxiliary section, the user can visually grasp the corresponding relation between the mutual connection destinations by referring to the installation written indicators. Hereinafter, FIGS. 24 to 34 show specific examples of the installation auxiliary section.

First Example

Figure 24:
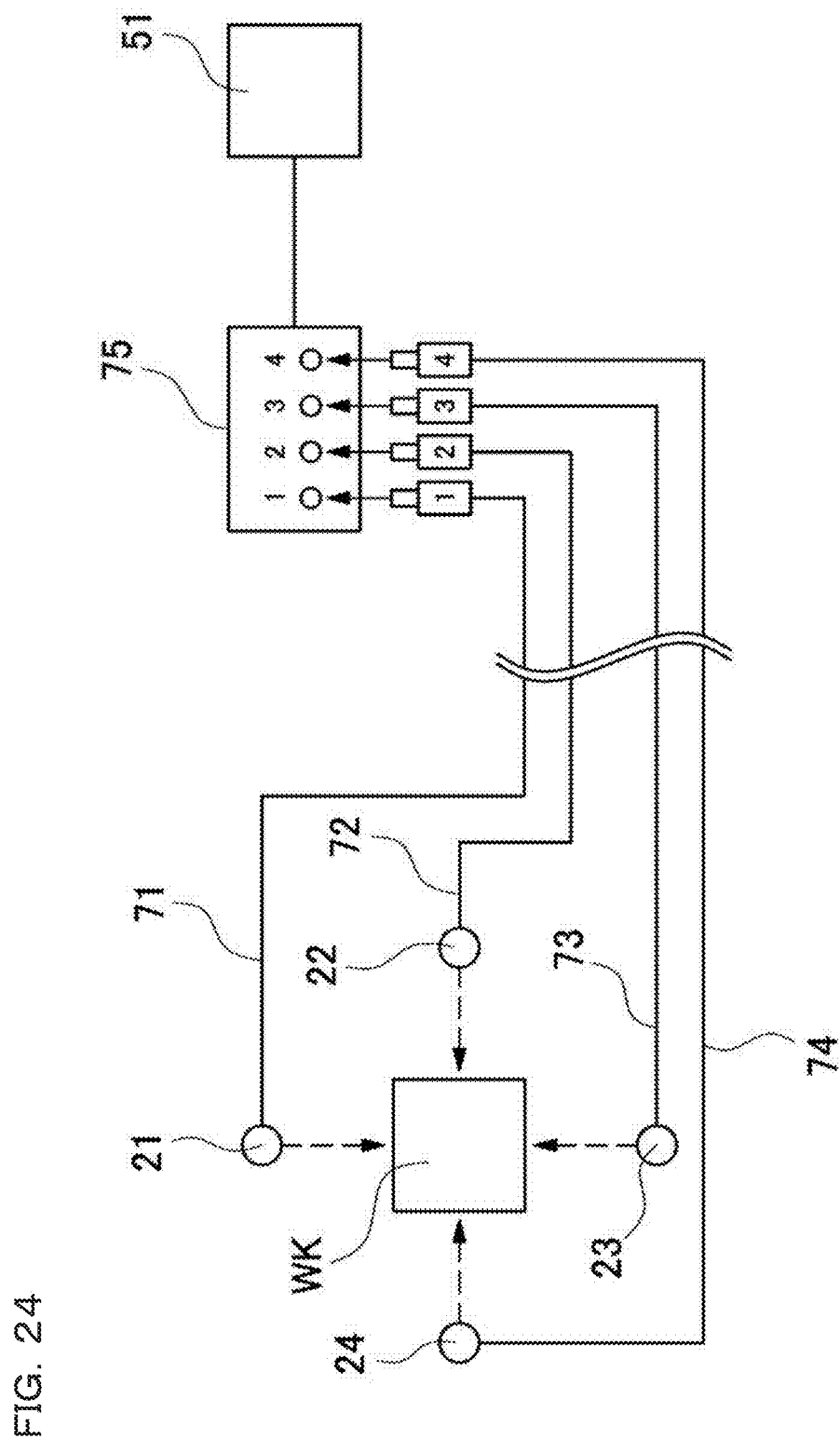
FIG. 24 is a schematic view showing an installation auxiliary section according to a first example.

FIG. 24 shows a state where a first illumination cable 71, a second illumination cable 72, a third illumination cable 73 and a fourth illumination cable 74, which are respectively extended from the first illumination section 21, the second illumination section 22, the third illumination section 23 and the fourth illumination section 24 shown in FIG. 2, are connected to the illumination dividing unit. The illumination dividing unit is provided with an illumination connector for connecting each of the illumination cables. By connecting the illumination cable to each of the illumination connectors, electricity is supplied from the illumination controlling section 31 at predetermined turning-on timing, to allow turning-on of the illumination section. In this case, when the illumination cable is erroneously connected to an illumination connector different from the original, a partial illumination image is captured in a different illumination direction or at different illumination timing, which results in preventing correct inspection from being performed. Therefore, by providing a first installation written indicator showing an illumination connector as a connection destination on the illumination connector as the installation auxiliary section, the illumination connector as the connection destination is shown to the user, to allow avoidance of erroneous connection. Here, "1" is indicated on the illumination connector as a connection destination of the first illumination cable 71, thereby allowing the user to visually confirm the connection destination of the first illumination section. Further, a second installation written indicator showing information on a connection destination is preferably provided also at the connection end of the illumination cable extended from each of the illumination sections. In the example of FIG. 24, "1" is indicated as the second installation written indicator at the connection end of the first illumination cable extended from the first illumination section. It is thereby possible for the user to associate "1" on the illumination connector with "1" on the first illumination cable and connect them, so as to ensure the accuracy of the connection. In such a manner, by matching the first installation written indicator provided on the illumination connector with the second installation written indicator provided on the connection cable, it is possible to further reduce errors in the connection operation and improve the reliability of the inspection. Similarly, each of the second illumination cable 72, the third illumination cable 73 and the fourth illumination cable 74 can be provided with the second installation written indicator, and the illumination connectors as connection destinations of the cables can also be provided with first installation written indicators. As described above, the illumination dividing unit and the illumination controlling section may be integrated.

Figure 25:
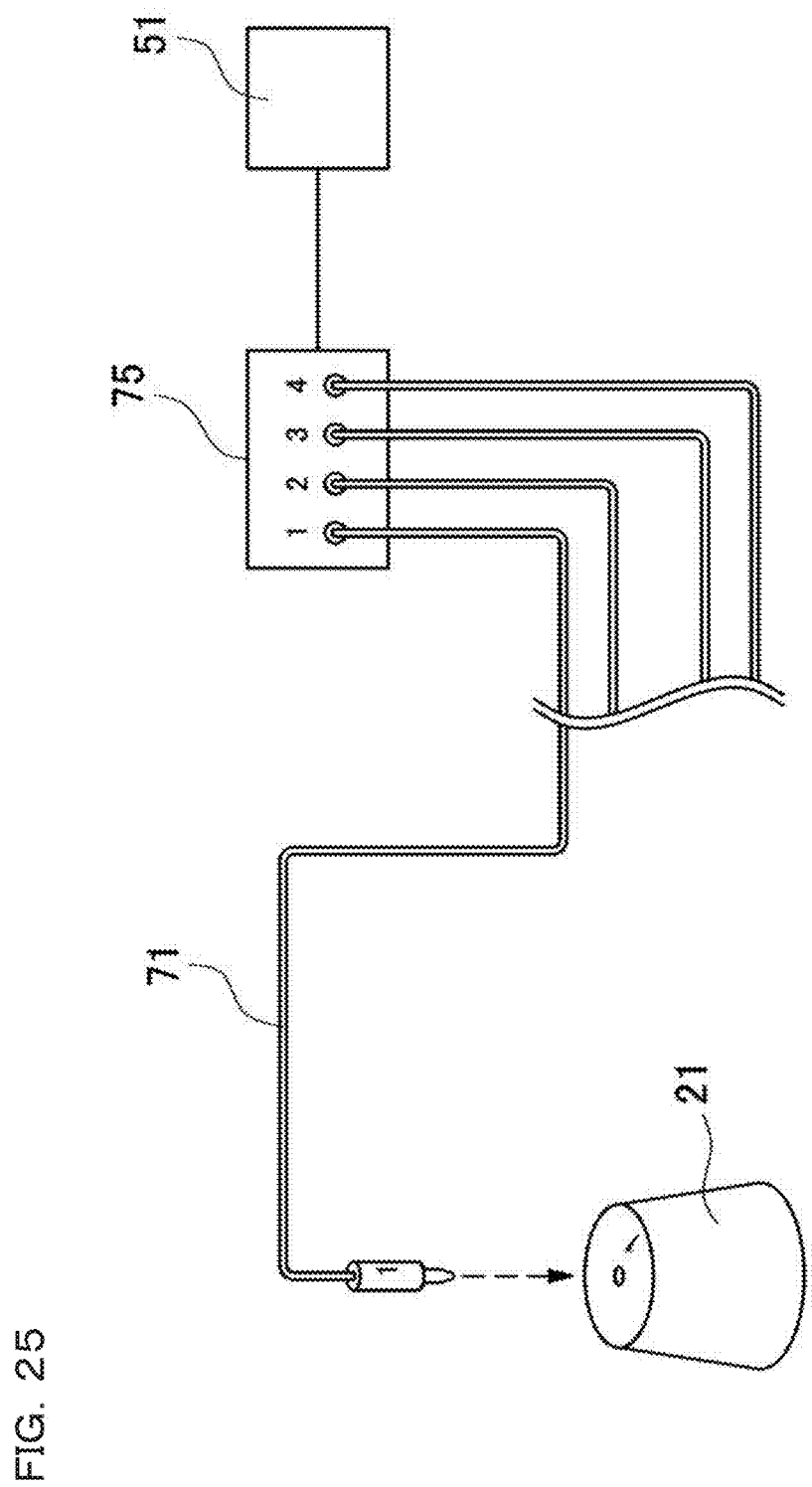
FIG. 25 is a schematic view showing an example where the installation auxiliary section has been applied to connection between an illumination cable and the illumination section.
Figure 26:
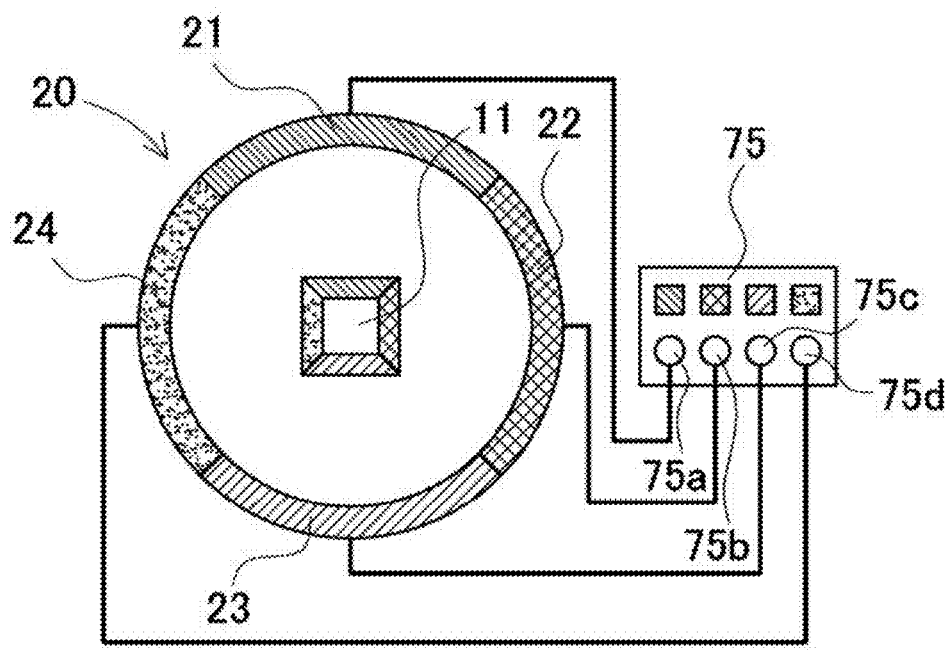
FIG. 26 is a schematic view showing an installation auxiliary section according to a second example.

The installation auxiliary section is also applicable to connection between the illumination cable and the illumination section. That is, as shown in FIG. 25, also in an interface portion that connects the first illumination cable 71 to the first illumination section, an installation written indicator showing the corresponding relation of wiring as the installation auxiliary section may be provided. Here, "1" is indicated as a third installation written indicator on a connector portion of the first illumination section to be connected with the first illumination cable. Further, "1" is also indicated at the end edge of the first illumination cable. Accordingly, also at the time of the wiring operation for the first illumination section and the first illumination cable, mix-up of wiring can be avoided. Especially when a plurality of illumination sections have the same shape or the illumination cable is long, in other words, even in an environment where a wiring error is apt to occur, it is possible to reliably perform wiring and enhance the reliability of the inspection accuracy. In the example of FIG. 25, only the connection between the first illumination section and the first illumination cable is shown for simplifying the drawing, but it goes without saying that the same applies to the second illumination section to the fourth illumination section. Further, although each illumination cable is an insertion type with respect to the illumination section and the illumination dividing unit in the above example, even in a configuration where the illumination cable is directly connected to the illumination section or the illumination dividing unit, the present embodiment can be applied. Further, although the number has been used as the installation written indicator in the above example, a visible written indicator such as a letter, a symbol, a mark or a color is applicable as appropriate. Further, a plurality of written indicators may be combined. For example, when a color and a number is combined to constitute an installation written indicator, such as 1 in red, 2 in blue, 3 in green and 4 in purple, the wiring relation becomes clearer. Furthermore, the installation written indicator is not restricted to a visible one, but in addition to or in place of this, an installation written indicator recognizable by the sense of touch, such as Braille, may be applied. It is preferably usable especially when the connection portion is minute or printing and marking are physically difficult, or when visible confirmation is difficult such as the case of installation in a narrow place or a dark place.

Second Example

In the above example, there has been described the example of supporting the operation to wire each of the illumination sections to the illumination controlling section by the installation auxiliary section. In this case, the installation auxiliary section is provided on each of the illumination sections and the illumination cable. However, the installation auxiliary section is not restricted to this, and is applicable to supporting an operation of installing the illumination section at a correct position. In this case, the installation auxiliary section can be provided on each of the imaging section and the illumination section. Such an example is shown in a schematic plan view of FIG. 26. In this example, the first illumination section 21, the second illumination section 22, the third illumination section 23 and the fourth illumination section 24, each being formed in an arc shape, are arranged around (here, to the north, south, east and west of) the imaging section in a plan view. As described above, when the shape of each of the illumination sections is the same, mix-up can occur at the time of installing the illumination sections. Therefore, by providing a written indicator for arrangement of the illumination section as the installation auxiliary section on the imaging section, it is possible to perform arrangement in accordance with this written indicator, and avoid mix-up. Here, the top surface of each of the illumination sections is colored differently, and the same color is also used for a fourth installation written indicator on a region of the top surface of the imaging section which corresponds to each of the illumination sections. In this example, the first illumination section 21 is colored in red, the second illumination section 22 is colored in blue, the third illumination section 23 is colored in green, and the fourth illumination section 24 is colored in purple. This allows the user to distinguish the illumination sections in accordance with the fourth installation written indicators provided on the imaging section at the time of the installation operation for the illumination sections, and further facilitates the user to visually confirm whether or not the illumination sections have been correctly installed after the installation. Thus, it is possible to obtain an advantage that a mix-up error of the illumination sections can be prevented.

This is one example, and a color to be used on each of the illumination sections can be arbitrarily changed. Moreover, the color is not restrictive, and the discrimination is also possible by means of written indicators such as a pattern, a design, a symbol, a number or a character.

Further, a position where such a written indicator is provided can be the side surface or the bottom surface of each of the illumination sections and the imaging section, other than the top surface thereof. Moreover, the configuration where the installation auxiliary section is provided on the imaging section is not restrictive, and for example, the installation auxiliary section may be provided on another region such as a stage on which workpiece is placed, or a casing for the image inspection apparatus.

Also in the operation of wiring the illumination cable pulled out from each of the illumination sections and the illumination dividing unit, it is possible to indicate correct combination of wiring destinations by the installation auxiliary section similarly to the above, thereby to prevent an error in the wiring operation and further to facilitate performing the confirmation operation after the wiring.

Third Example

Figure 27:
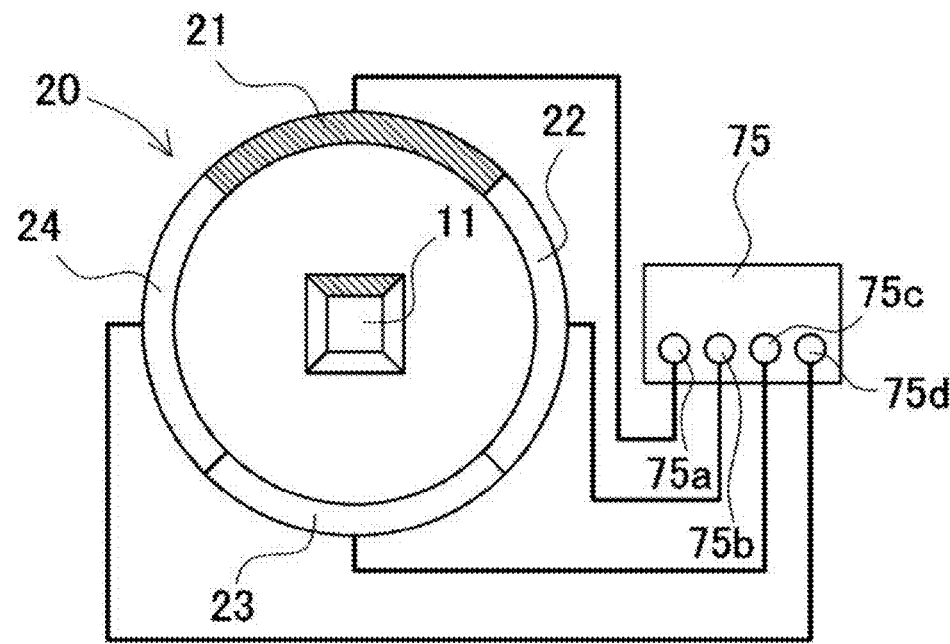
FIG. 27 is a schematic view showing an installation auxiliary section according to a third example.

In the above second example, there has been described the example where the relative installation positions at the time of annularly arranging three or more illumination sections around the workpiece are confirmed by the installation auxiliary section. The illumination sections can also be integrally configured in advance as an annular illumination unit as described above. Also in such a case, as shown in FIG. 23, unless the annular illumination unit 20 is fixed by adjusting its relative rotational position, namely rotational angle, with respect to the imaging section, an accurate result of the photometric stereo processing cannot be obtained. Especially when the annular illumination unit 20 has a point-symmetric shape, a rotational position is not decided, thus making the adjustment operation difficult. Even in such a case, the relative rotational positions of the annular illumination unit and the imaging section can be positioned by the installation auxiliary section. For example, as shown in FIG. 27, lines or joints are indicated as the installation auxiliary section on boundary portions of the first illumination section 21, the second illumination section 22, the third illumination section 23 and the fourth illumination section 24 which constitute the annular illumination unit 20. This clarifies a region occupied by each of the illumination sections. Further, this is also made to correspond to the imaging section, and lines are indicated on its top surface. Providing such an installation auxiliary section facilitates defining the rotational positions of the imaging section and the annular illumination unit 20 and further facilitates performing positioning thereof.

Even when the annular illumination unit 20 is rotated in units of 45°, it cannot be discriminated, and hence a position as a reference is clarified. For example, coloring the first illumination section clarifies the attitude of the annular illumination unit 20, and it is thus possible to avoid a circumstance of displacement in units of 45°. Further, a region of the top surface of the imaging section which corresponds to the colored first illumination section is preferably colored in a similar manner. Therefore, matching the colored regions with each other facilitates determining the rotational angle of the annular illumination unit.

The above is one example, and as for the installation auxiliary section, another written indicator which defines the rotational position of the annular illumination unit can be adopted as appropriate. For example, as in a modified example shown in FIG. 28, a line is indicated in advance at a position to become a reference of the annular illumination unit 20, and it is defined in advance such that this line is located at a zenith, thereby allowing accurate positioning of even the annular illumination unit 20 having a point-symmetric shape. Further, as the written indicator showing the reference position is not restricted to the line, but an arbitrary pattern such as another mark, a character or a design can be used. For example, in the example of FIG. 29, a position to become a zenith is indicated by an arrow.

Figure 30:
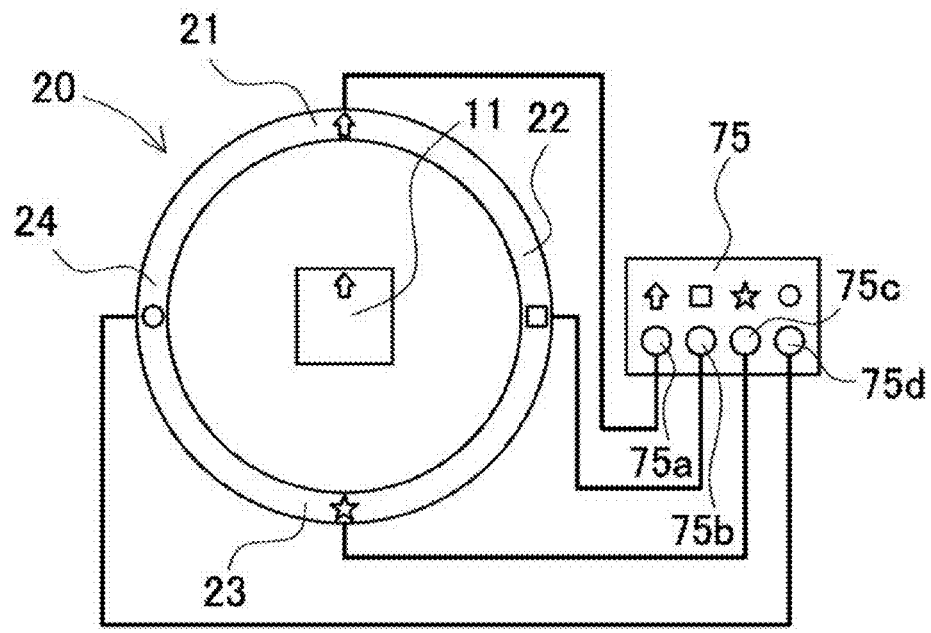
FIG. 30 is a schematic view showing an installation auxiliary section according to another modified example.
Figure 31:
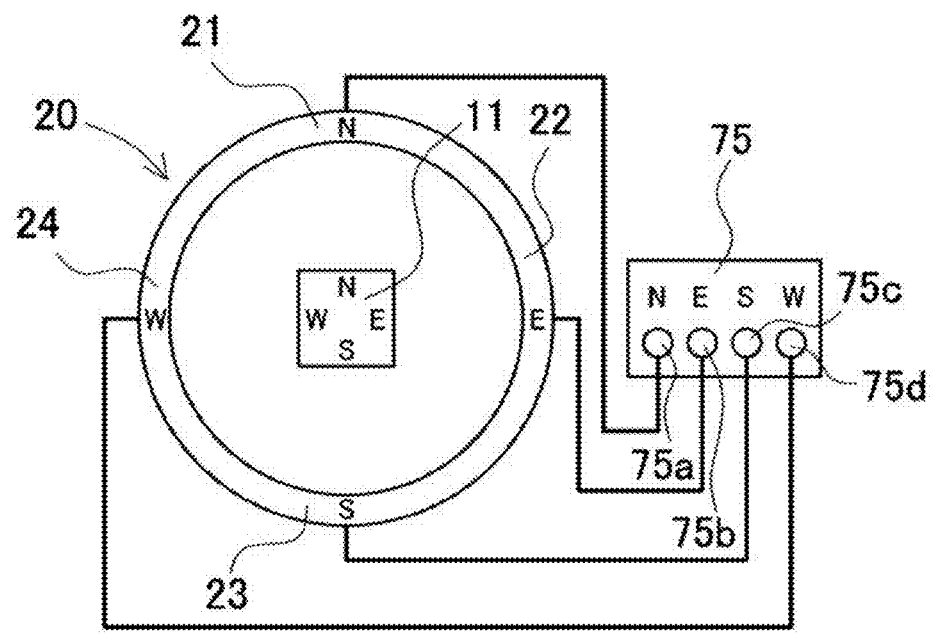
FIG. 31 is a schematic view showing an installation auxiliary section according to another modified example.

The number of reference positions is not restricted to one, and a plurality of reference positions may be provided. For example, as shown in FIG. 30, a different mark may be indicated in a region corresponding to each of the illumination sections. Further, indication of a similar mark to each of these marks on the illumination connector of the illumination dividing unit can also be used to discriminate wiring of the illumination cable pulled out from each of the illumination sections.

The written indicator is not restricted to the mark, and an arbitrary pattern such as a character, a color or a design can be used. For example, in the example shown in a plan view of FIG. 31, characters N, E, S and W showing the cardinal directions are indicated. Further, similar characters showing the cardinal directions are also added to the imaging section 11 and the illumination dividing unit 75. This can facilitate positioning and wiring in accordance with the setting of the photometric stereo processing.

Figure 32:
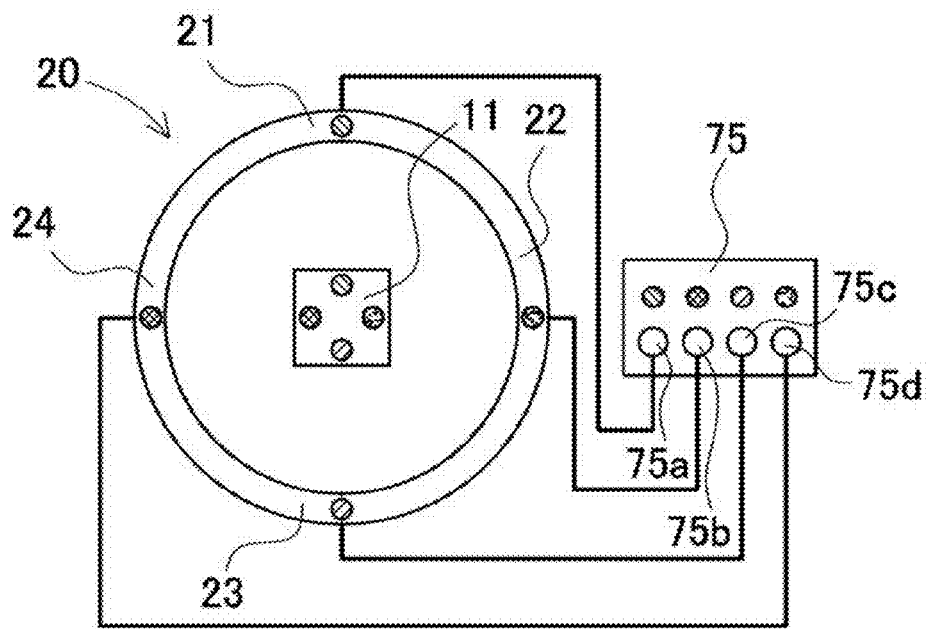
FIG. 32 is a schematic view showing an installation auxiliary section according to another modified example.
Figure 33:
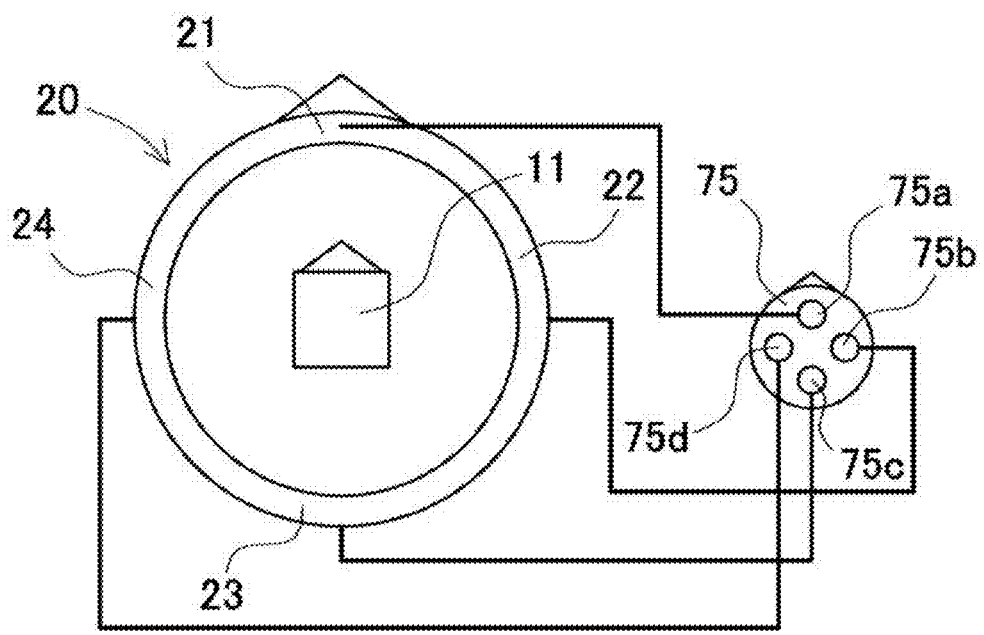
FIG. 33 is a schematic view showing an installation auxiliary section according to another modified example.
Figure 34:
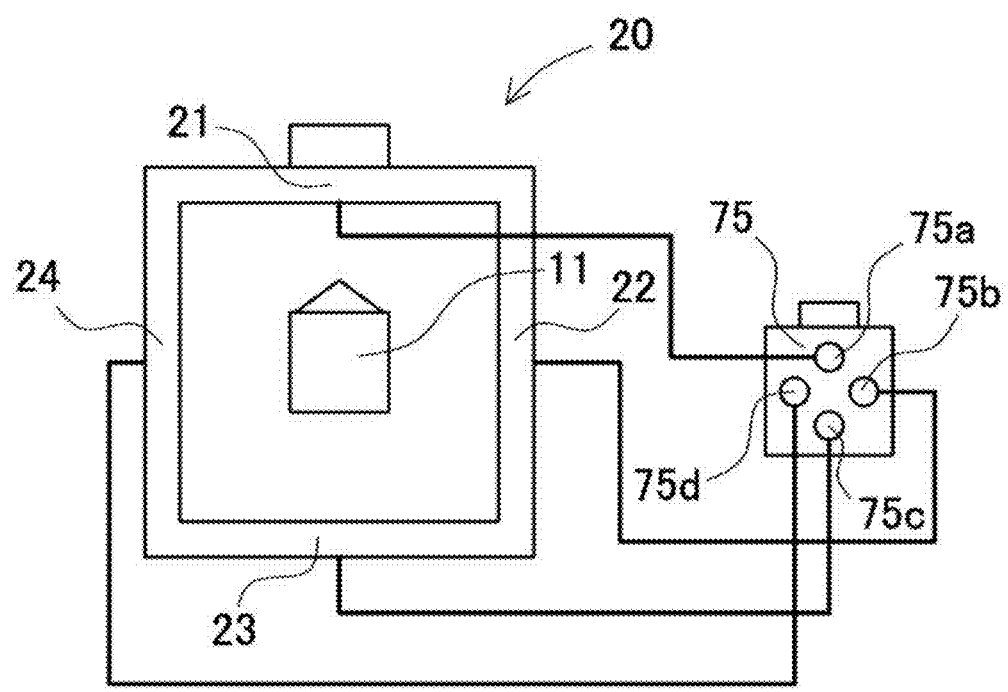
FIG. 34 is a schematic view showing an installation auxiliary section according to another modified example.

In the example shown in a plan view of FIG. 32, a colored mark is indicated in a region corresponding to each of the illumination sections. In this example, the first illumination section 21 is provided with a red mark, the second illumination section 22 with a blue mark, the third illumination section 23 with a green mark, and the fourth illumination section 24 with a purple mark. Further, providing the similar marks to the imaging section 11 and the illumination dividing unit 75 can facilitate performing the positioning and wiring operations and the confirmation.

Moreover, as the method for determining a reference position, there can also be adopted a method for eliminating a physical shape by means of a point-symmetric shape to clarify an attitude from an external shape, other than the configuration where a written indicator showing a reference is provided. For example, in the example shown in FIG. 33, it is configured such that a projection having a triangle shape is provided in part of the annular illumination unit 20, and is set at a zenith position as a reference, thereby to allow positioning. Further, forming similar projections in the imaging section 11 and the dividing unit 75 allows matching of attitudes and wiring thereof. Moreover, each of the shapes of each of the illumination sections 21 to 24 and the illumination dividing unit 75 is not restricted to a circle in a plan view, but an arbitrary shape such as a rectangular shape or a polygonal shape can be used. For example, in the example shown in FIG. 34, a rectangular shape is used. Further, it is adequate that the projection can serve as a sign showing a position or a direction as a reference and can employ an arbitrary form such as a depression.

Figure 28:
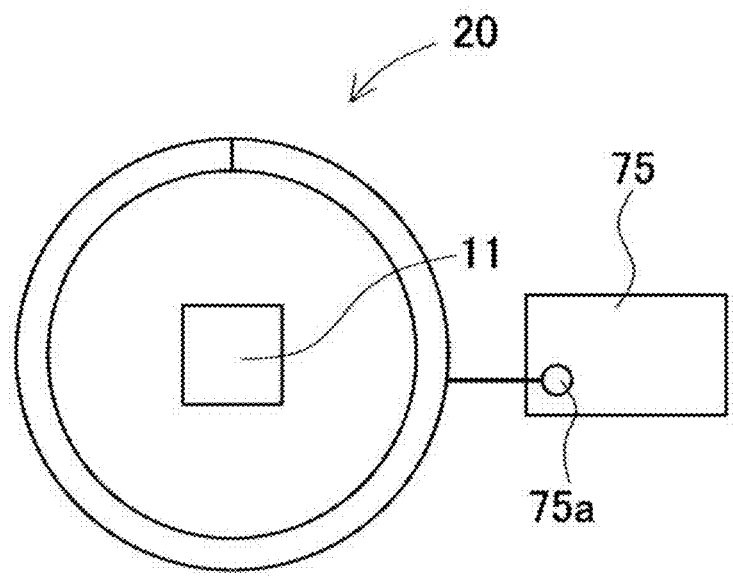
FIG. 28 is a schematic view showing an installation auxiliary section according to a modified example.
Figure 29:
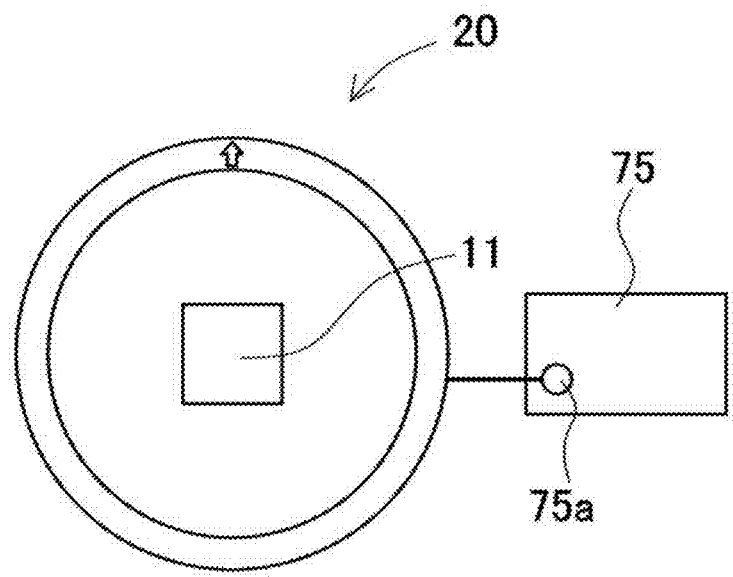
FIG. 29 is a schematic view showing an installation auxiliary section according to another modified example.

In the example of FIG. 27 described above, the illumination cable is pulled out from the annular illumination unit 20 formed by integrating the first illumination section 21, the second illumination section 22, the third illumination section 23 and the fourth illumination section 24, by being made to correspond to each of the illumination sections, but the illumination cables may be put together in the integrated annular illumination unit 20. This can save labor for the wiring operation, avoid mix-up, and further simplify the wiring itself. FIGS. 28 and 29 show examples of such wiring.

(Image Inspection Method)

A procedure of an image inspection method for performing visual inspection of the workpiece will be described using the image inspection apparatus 1 with reference to a flowchart of FIG. 35.

In Step ST1, the image processing part 41 issues a trigger signal to each of the illumination sections 21, 22, 23, 24 via the illumination controlling section 31, and the illumination sections 21, 22, 23, 24 are turned on one by one in accordance with the trigger signal.

In Step ST2, the imaging section 11 is activated every time each of the illumination sections 21, 22, 23, 24 is turned on, to capture an image of the workpiece WK.

In Step ST3, the imaging section 11 transmits four image signals Q1 to Q4 of the captured images of the workpiece WK to the image processing part 41.

In Step ST4, by use of the four image signals Q1 to Q4 inputted from the imaging section 11, the image processing part 41 calculates a normal vector of the surface at each pixel with respect to each of the image signals Q1 to Q4.

In Step ST5, the image processing part 41 creates reduced inclination images respectively obtained by reducing the image into 1/1, 1/2, 1/4, 1/8, 1/16 and 1/32, which will be required in post-stage processing, with respect to each of the image signals Q1 to Q4. Further, the image processing part 41 previously creates a texture extraction image, which will be required in the post-stage processing, with respect to each of the image signals Q1 to Q4.

In Step ST6, a characteristic size is adjusted according to the need. By changing the characteristic size, a size of roughness extracted in a roughness extraction image changes. Specifically, when the characteristic size is made large, there is obtained a roughness extraction image where roughness having a large size is extracted. On the contrary, when the characteristic size is made small, roughness having a small size is extracted. Therefore, the user adjusts the characteristic size in accordance with a size of a flaw to be extracted. Alternatively, in the case of the use for OCR, a roughness extraction image suitable for OCR can be obtained by increasing the characteristic size.

In Step ST7, calculation of a roughness extraction image is performed. In this example, the image processing part 41 generates a roughness extraction image where roughness is extracted in accordance with the characteristic size set in Step ST6, and displays the roughness extraction image on the display section 51.

In Steps ST10 to 12, the image processing part 41 or the PLC 81 performs, on a contour extraction image, flaw detection processing for detecting a flaw by use of a flaw inspection tool, to perform flaw determination processing for determining whether or not to have detected a flaw.

First, in Step ST10, the image processing part 41 or the PLC 81 specifies a position of an inspection region to become an inspection target with respect to a generated contour image. At the time of setting the inspection region, an image of the workpiece WK is extracted by, for example, extracting an edge. When the workpiece WK is not greatly displaced, a setting position for the inspection region may be registered in advance.

In Step ST11, the image processing part 41 or the PLC 81 performs image processing for detecting a flaw in the specified inspection region. The image processing part 41 or the PLC 81 calculates a reference concentration value by a stored calculation method, and calculates a difference between the reference concentration value and a concentration value of each pixel in the inspection region with respect to each pixel. Then, the image processing part 41 or the PLC 81 executes labeling processing (processing of attaching labels with "0, 1, 2, . . . " to groups of white pixels in a binary image) by means of a set and stored threshold (a threshold referred to as a flaw amount is decided in advance), to calculate a characteristic amount with respect to each specified flaw. The calculated characteristic amount is, for example, plus/minus information on plus/minus of differences, a total of differences, the maximum value of differences, an average value of differences, or a standard deviation of differences.

In Step ST12, the image processing part 41 or the PLC 81 executes the flaw determination processing on the flaw specified in Step ST11 in accordance with a determination reference used for flaw determination. When it is determined as a flaw, a place of the flaw is marked on the display section 51, and the processing is completed.

Modified Example

In the above example, there has been described the example where, by making a characteristic size adjustable by the user, a roughness extraction image in which roughness with a size desired by the user is extracted is generated by means of a parameter of the characteristic size. However, the present invention is not restricted to this configuration, and by preparing a plurality of observation modes in accordance with the use for observation or a purpose of the user and allowing the user to select an observation mode, it is possible to form such a configuration as to generate a desired image. Such an example will be described with reference to a flowchart of FIG. 36. Steps ST"1 to ST"5 are similar to those in FIG. 35, and hence detailed descriptions thereof will be omitted.

In Step ST"6, the user is allowed to select an observation mode. In this example, any of a contour extraction mode, a texture extraction mode and a roughness mode is made selectable. In each observation mode, a characteristic size suitable for observation is preset. The user may manually adjust the characteristic size finely after selecting the observation mode. The following step differs depending on the selected observation mode. That is, the process proceeds to Step ST"7 when the contour extraction mode is selected, the process proceeds to Step ST"8 when the texture extraction mode is selected, and the process proceeds to Step ST"9 when the roughness mode is selected. The process proceeds to Step ST"10 after the processing in each step. In such a manner, the roughness extraction image generating section, the contour image generating section 41*b* and the texture extraction image generating section 41*c* are switchable.

In Step ST"7, the image processing part 41 performs calculation of a roughness extraction image. That is, the image processing part 41 displays on the display section 51 a contour extraction image with a characteristic size for a roughness extraction image to be displayed.

In Step ST"8, the image processing part 41 executes the processing in the case of the contour extraction mode having been selected by the user. That is, the image processing part 41 performs calculation of a contour extraction image based on the reduced inclination image created in Step ST"5, and displays the contour extraction image on the display section 51.

In Step ST"9, the image processing part 41 executes the processing in the case of the texture extraction mode having been selected by the user. That is, the image processing part 41 performs calculation of a contour extraction image based on the texture extraction image created in Step ST"5, and displays the texture extraction image on the display section 51.

Figure 35:
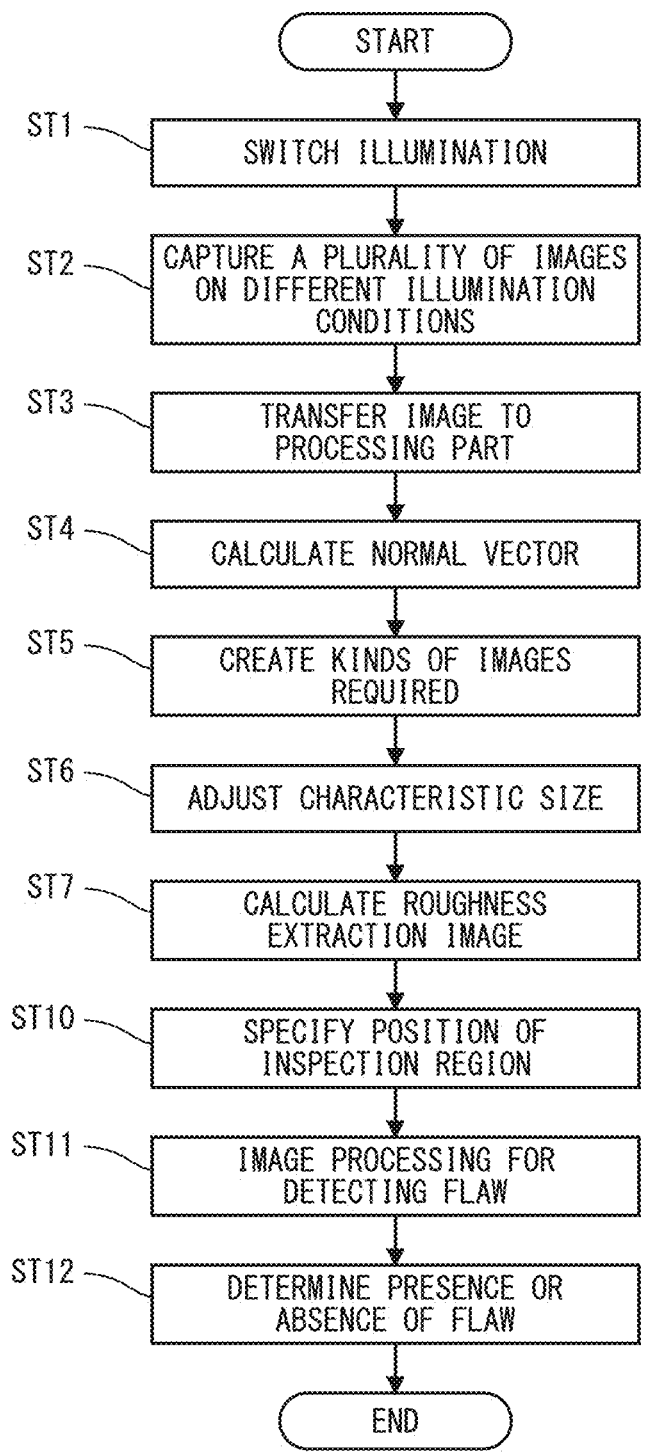
FIG. 35 is a flowchart showing an image inspection method according to an example.
Figure 36:
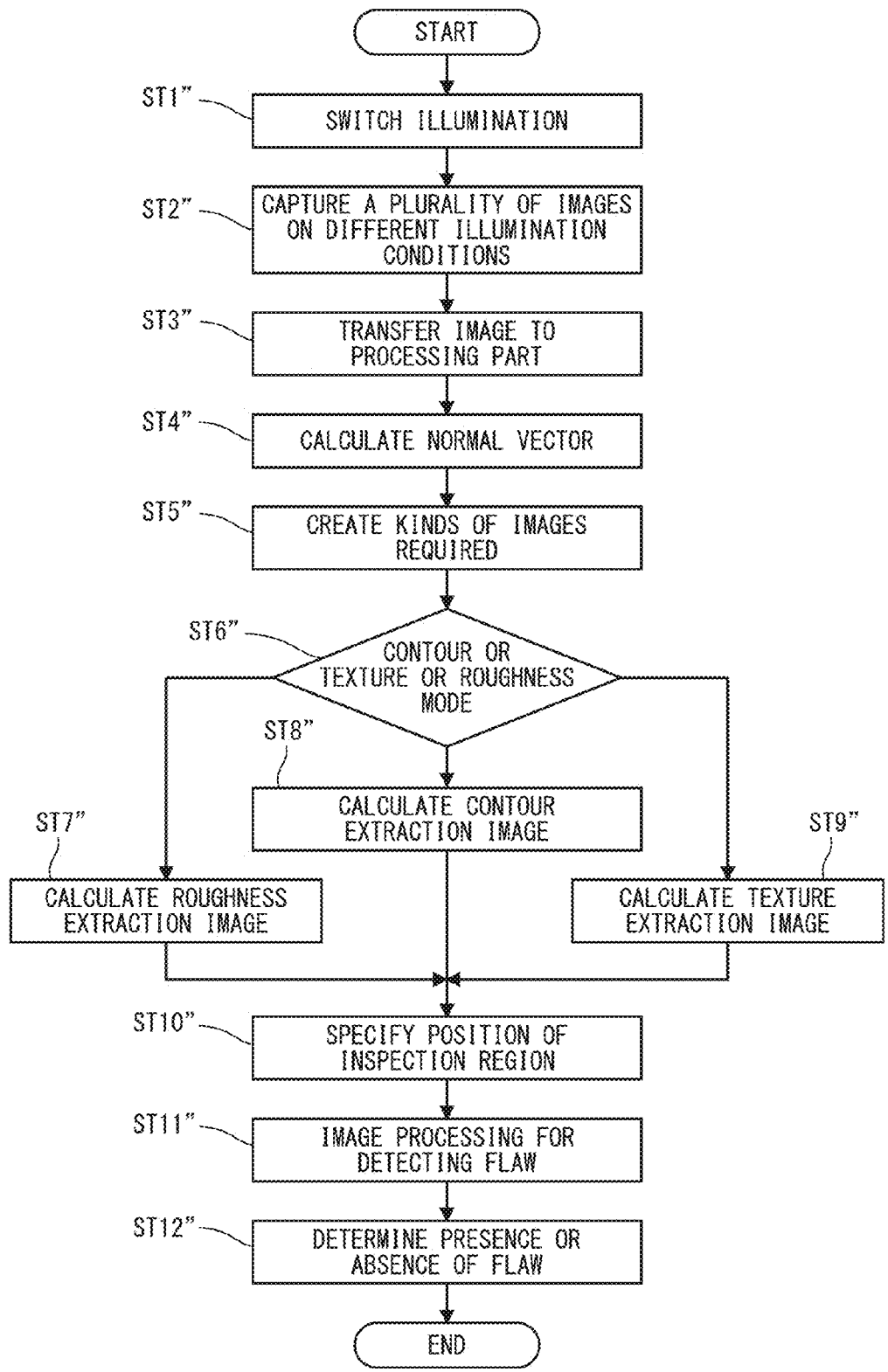
FIG. 36 is a flowchart showing an image inspection method according to a modified example.

For subsequent Steps ST"10 to ST"12, a similar procedure to that in FIG. 35 described above can be used, and detailed descriptions thereof will be omitted.

According to the above image inspection apparatus, although a primary inclination image is generated by the photometric stereo method at first, a secondary inclination image, namely a contour extraction image is created by performing differential processing on the generated primary inclination image in the X-direction and the Y-direction. By this processing, it is possible to reduce a disadvantage of the photometric stereo method like a conventional one in which the obtained inspection image greatly changes by slight inclination of illumination or the installation surface of the workpiece or an error of input information such as an originally inputted illumination position, and an inspection image corresponding to an actual object cannot be obtained, for example as in a phenomenon where a roughness image is obtained although there is actually no roughness, and a phenomenon where an image in which the center of the workpiece WK is swollen is obtained because of the tendency that a place closer to the illumination is normally brighter. By setting a tone with which a place where a change in inclination is large in a depression direction of the surface becomes dark and setting a tone with which a place where a change in inclination is small in a projection direction of the surface becomes bright, there is obtained an image preferable for extracting a flaw, a contour and the like where inclination of the surface of the workpiece greatly changes.

Further, the contour image generating section creates a plurality of reduced inclination images with a different reduction ratio from the calculated normal vector at each of the pixels, performs differential processing in the X-direction and the Y-direction on each of the reduced inclination images, performs weighting such that a reduced contour image with a predetermined reduction ratio is greatly reflected to the obtained reduced contour image, to enlarge the image to an original size. All the reduced contour images thus enlarged are added to form a contour extraction image. According to the above configuration, although a size used for flaw determination varies depending on the use of the user, weighting can be performed such that a reduced contour image with a predetermined reduction ratio is greatly reflected to a contour extraction image. Thus, a contour extraction image where a reduced contour image with a reduction ratio desired by the user is emphasized can be obtained in accordance with the use of the user. As a demand, user may judge a depression over ten pixels as a flaw or may judge a depression over 100 pixels as a flaw. Further, only a steep edge may be extracted as an edge.

Further, a flaw is normally detected over a plurality of frequencies. Since the contour extraction image which is obtained by adding all the enlarged reduced contour images is employed, a flaw, a contour and the like can be clearly detected without blur as a whole as compared to a reduced contour image with only one frequency.

Further, the weighting can be performed by preparing a previously decided weighting set, and applying the weighting set to the reduced contour image, to proportionally divide an adoption ratio of the reduced contour image with each of the reduction ratios. With this configuration, the weighting set (characteristic size) previously decided is preset at the time of synthesis with a contour extraction image, and hence the user can instantly and easily perform switching to a desired contour extraction image.

The weighting set can include a set that makes large an adoption ratio of a reduced contour image by which a contour extraction image with clear roughness of the surface of the workpiece is obtained. By taking this way to use as, for example, the roughness mode, it can be separately used from the contour extraction mode.

Further, since the weighting set can include a set that makes large an adoption ratio of a reduced contour image by which a contour extraction image suitable for OCR is obtained, it is possible to create an image preferable for performing OCR on a carved seal in cast metal, for example.

Further, there is formed a configuration where, from a calculated normal vector at each of the pixels which exists in number corresponding to the number of times of illumination performed by the illumination sections, albedos of each of the pixels in the same number as the number of the normal vectors is calculated, to generate from the albedos a texture extraction image that shows a design obtained by removing an inclined state of the surface of the workpiece, thereby making the contour image generating section and the texture extraction image generating section switchable. Accordingly, although it has been required to search for a place where a flaw should not exist and decides the place an inspection region since it is normally difficult to discriminate an original flaw and an originally existing contour, it is possible to perform the flaw inspection after performing search in a texture extraction image and deciding an inspection region. Moreover, also at the time of performing OCR, it is possible to perform OCR after performing search in a texture extraction image and deciding a target region for performing OCR.

The texture extraction image generating section can sort values of the albedos of each of the pixels in the same number as the number of the normal vectors, and employs, as the texture extraction image, an image formed by adopting a pixel value in a specific order from the top. Accordingly, a pixel value with high luminance where halation has occurred is not adopted, and a texture extraction image with an influence of halation removed therefrom is obtained.

Further, although it is generally common understanding that the photometric stereo technique is a technique for three-dimensional measurement, by providing a flaw inspection tool required for the flaw inspection after generation of a contour extraction image, it is possible to provide an image inspection apparatus that can be considered as a practical product obtained by applying the photometric stereo technique to the flaw inspection.

Further, the image inspection apparatus includes: an imaging section for capturing an image of a workpiece from a certain direction; an illumination section for illuminating the workpiece from different directions at least three times; an illumination controlling section for sequentially turning on the illumination section one by one; an image generating section for driving the imaging section at each illumination timing to generate a plurality of partial images; a normal vector calculating section for calculating a normal vector with respect to the surface of the workpiece at each of pixels by use of a pixel value of each of pixels having a corresponding relation among the plurality of images; and a texture extraction image generating section for calculating, from a calculated normal vector at each of the pixels which exists in number corresponding to the number of times of illumination performed by the illumination section, albedos of each of the pixels in the same number as the number of the normal vectors, to generate from the albedos a texture extraction image that shows a design obtained by removing an inclined state of the surface of the workpiece. The texture extraction image generating section can sort values of the albedos of each of the pixels in the same number as the number of the normal vectors, and employ, as the texture extraction image, an image formed by adopting a pixel value in a specific order from the top. With this configuration, the texture extraction image generating section sorts values of the albedos of each of the pixels in the same number as the number of the normal vectors, and employs an image formed by adopting a pixel value in a specific order from the top as the texture extraction image. Accordingly, a pixel value with high luminance where halation has occurred is not adopted, and a texture extraction image with an influence of halation removed therefrom is obtained.

As thus described, according to an image inspection apparatus of the embodiment, it is possible to inspect a flaw and a printed character of the workpiece in an easy and robust manner by the photometric stereo method.

The image inspection apparatus, the image inspection method, the image inspection program, and the computer-readable recording medium or the recording device according to the present invention are preferably usable for an inspection device or a digitalizer using photometric stereo.

What is claimed is:

1. An image inspection apparatus for performing visual inspection of a workpiece, the apparatus comprising:
   three or more illumination sections for illuminating the workpiece from mutually different illumination directions;
   an illumination controlling section for turning on the three or more illumination sections one by one in a turning-on order;
   an imaging section for capturing an image of the workpiece from a certain direction at illumination timing for turning on each of the illumination sections by the illumination controlling section, to capture a plurality of partial illumination images with different illumination directions;
   a normal vector calculating section for calculating a normal vector with respect to a surface of the workpiece at each of pixels by a photometric stereo method by use of a pixel value of each of pixels having a corresponding relation among the plurality of partial illumination images captured by the imaging section; and
   a contour image generating section for performing differential processing in an X-direction and a Y-direction on the normal vector at each of the pixels calculated by the normal vector calculating section, to generate a contour image that shows a contour of inclination of the surface of the workpiece.

2. The image inspection apparatus according to claim 1, wherein
   the contour image generating section creates a plurality of reduced inclination images with a different reduction ratio from the calculated normal vector at each of the pixels, performs differential processing in the X-direction and the Y-direction on each of the reduced inclination images, performs weighting such that a reduced contour image with a predetermined reduction ratio is reflected to the obtained reduced contour image to enlarge the image to an original size, and adds all the enlarged reduced contour images, to form a contour extraction image.

3. The image inspection apparatus according to claim 2, wherein the weighting is performed by preparing a previously decided weighting set, and applying the weighting set to the reduced contour image, to proportionally divide an adoption ratio of the reduced contour image with each of the reduction ratios.

4. The image inspection apparatus according to claim 3, wherein the weighting set includes a set that makes large an adoption ratio of a reduced contour image by which a contour extraction image with clear roughness of the surface of the workpiece is obtained.

5. The image inspection apparatus according to claim 3, wherein the weighting set includes a set that makes large an adoption ratio of a reduced contour image by which a contour extraction image suitable for OCR is obtained.

6. The image inspection apparatus according to claim 1, further comprising:
   an inspection region specifying section for specifying a position of an inspection region to become an inspection target with respect to the generated contour image;
   an image processing section for performing image processing for detecting a flaw within the inspection region specified by the inspection region specifying section; and
   a determination section for determining presence or absence of a flaw on the surface of the workpiece from result of the processing by the image processing section.

7. The image inspection apparatus according to claim 1, wherein the imaging section and each of the illumination sections are independent separate members, and are arranged at arbitrary positions.

8. The image inspection apparatus according to claim 1, wherein four illumination sections are provided.

9. The image inspection apparatus according to claim 1, wherein
   the three or more illumination sections are made up of a plurality of light-emitting elements arranged in an annular shape, and
   the illumination controlling section
      takes a predetermined number of adjacent light-emitting elements as a first illumination block, simultaneously turns on the light-emitting elements in the first illumination block, and turns off other light-emitting elements, to make a first illumination section function as first illumination from a first illumination direction,
      performs control so as to turn on a second illumination block, which is made up of a predetermined number of light-emitting elements and adjacent to the first illumination block, to constitute the second illumination block for performing illumination from a second illumination direction different from the first illumination direction, and
      performs control so as to turn on a third illumination block, which is made up of a predetermined number of light-emitting elements and adjacent to the second illumination block, to constitute the third illumination block for performing illumination from a third illumination direction different from the first illumination direction and the second illumination direction.

10. An inspection method for capturing an image of a workpiece to perform visual inspection, the method comprising the steps of:

illuminating the workpiece from three or more mutually different illumination directions by illumination sections, and capturing one partial illumination image with respect to each of the illumination directions by use of a common imaging section whose imaging direction and relative position with the illumination sections are adjusted in advance, to acquire a plurality of partial illumination images with different illumination directions;

calculating a normal vector with respect to the surface of the workpiece at each of pixels by a normal vector calculating section by use of a pixel value of each of pixels having a corresponding relation among the plurality of partial illumination images with different illumination directions;

performing differential processing in an X-direction and a Y-direction on the calculated normal vector at each of the pixels, to generate a contour image that shows a contour of inclination of the surface of the workpiece by a contour image generating section; and performing visual inspection of the workpiece by use of the contour image.

11. An image inspection program embedded in a non-transitory computer readable medium for capturing an image of a workpiece to perform visual inspection, wherein the program allows a computer to realize functions of;

illuminating the workpiece from three or more mutually different illumination directions by illumination sections, and capturing one partial illumination image with respect to each of the illumination directions by use of a common imaging section whose imaging direction and relative position with the illumination sections are adjusted in advance, to acquire a plurality of partial illumination images with different illumination directions;

calculating a normal vector with respect to the surface of the workpiece at each of pixels by a normal vector calculating section by use of a pixel value of each of pixels having a corresponding relation among the plurality of partial illumination images with different illumination directions;

performing differential processing in an X-direction and a Y-direction on the calculated normal vector at each of the pixels, to generate a contour image that shows a contour of inclination of the surface of the workpiece by a contour image generating section; and performing visual inspection of the workpiece by use of the contour image.

12. A non-transitory computer-readable recording medium, in which the image inspection program according to claim 11 is recorded.

* * * * *

UNITED STATES PATENT AND TRADEMARK OFFICE
CERTIFICATE OF CORRECTION

PATENT NO. : 9,632,036 B2
APPLICATION NO. : 14/716901
DATED : April 25, 2017
INVENTOR(S) : Sun It is certified that error appears in the above-identified patent and that said Letters Patent is hereby corrected as shown below:

On the Title Page

Under abstract "12 Claims, 28 Drawing Sheets" should read -- 14 Claims, 28 Drawing Sheets --.

In the Claims

Column 36, Line 26 (approx.), add the following:

-- 13. The image inspection apparatus according to claim 1, further comprising:
a texture extraction image generating section for calculating, from a normal vector at each of the pixels which exists in number corresponding to the number of times of illumination performed by the illumination sections and is calculated by the normal vector calculating section, albedos of each of the pixels in the same number as the number of the normal vectors, to generate from the albedos a texture extraction image that shows a design obtained by removing an inclined state of the surface of the workpiece,
wherein the contour image generating section and the texture extraction image generating section are switchable.

14. The image inspection apparatus according to claim 13, wherein the texture extraction image generating section sorts values of the albedos of each of the pixels in the same number as the number of the normal vectors, and employs, as the texture extraction image, an image formed by adopting a pixel value in a specific order from the top. --.

Signed and Sealed this
Twenty-third Day of May, 2017

Michelle K. Lee
*Director of the United States Patent and Trademark Office*